US011000633B2

United States Patent
Gonçalves Dos Reis et al.

(10) Patent No.: US 11,000,633 B2
(45) Date of Patent: May 11, 2021

(54) URETERAL STENT, METHODS AND USES THEREOF

(71) Applicant: ASSOCIATION FOR THE ADVANCEMENT OF TISSUE ENGINEERING AND CELL BASED TECHNOLOGIES AND THERAPIES—A4TEC, Braga (PT)

(72) Inventors: Rui Luis Gonçalves Dos Reis, Oporto (PT); Ana Rita Cruz Duarte, Braga (PT); Alexandre António Antunes Barros, Braga (PT); Estêvão Augusto Rodrigues De Lima, Oporto (PT); Carlos André Ribeiro Oliveira, Guimarães (PT); Jorge Manuel Nunes Correia Pinto, Oporto (PT)

(73) Assignee: ASSOCIATION FOR THE ADVANCEMENT OF TISSUE ENGINEER, Braga (PT)

( * ) Notice: Subject to any disclaimer, the term of this patent is extended or adjusted under 35 U.S.C. 154(b) by 5 days.

(21) Appl. No.: 15/574,046

(22) PCT Filed: May 17, 2016

(86) PCT No.: PCT/IB2016/052875
§ 371 (c)(1),
(2) Date: Nov. 14, 2017

(87) PCT Pub. No.: WO2016/181371
PCT Pub. Date: Nov. 17, 2016

(65) Prior Publication Data
US 2018/0296734 A1    Oct. 18, 2018

(30) Foreign Application Priority Data

May 14, 2015   (PT) .......................... 108476
May 26, 2015   (EP) ........................ 15169249
Jan. 29, 2016   (PT) .......................... 109122

(51) Int. Cl.
| | | |
|---|---|---|
| A61L 31/04 | (2006.01) | |
| A61L 31/10 | (2006.01) | |
| A61L 31/14 | (2006.01) | |
| A61L 31/16 | (2006.01) | |
| B29C 45/00 | (2006.01) | |
| B29C 71/00 | (2006.01) | |
| A61F 2/04 | (2013.01) | |
| B29L 31/00 | (2006.01) | |

(52) U.S. Cl.
CPC ........... *A61L 31/041* (2013.01); *A61L 31/042* (2013.01); *A61L 31/045* (2013.01); *A61L 31/10* (2013.01); *A61L 31/148* (2013.01); *A61L 31/16* (2013.01); *B29C 45/0001* (2013.01); *B29C 71/0009* (2013.01); *A61F 2/04* (2013.01); *A61F 2002/048* (2013.01); *A61F 2240/001* (2013.01); *A61F 2250/0067* (2013.01); *A61F 2250/0096* (2013.01); *A61L 2430/22* (2013.01); *B29K 2089/00* (2013.01); *B29L 2031/753* (2013.01)

(58) Field of Classification Search
CPC .... A61L 31/041; A61L 31/045; A61L 31/042; A61L 31/16; A61L 31/10; A61L 31/148; A61L 2430/22; B29C 45/0001; B29C 71/0009; A61F 2/04; A61F 2002/048; A61F 2240/001; A61F 2250/0067; A61F 2250/0096; B29K 2089/00; B29L 2031/753
See application file for complete search history.

(56) References Cited

U.S. PATENT DOCUMENTS

| | | | |
|---|---|---|---|
| 6,368,356 B1 | 4/2002 | Zhong et al. | |
| 7,794,494 B2 * | 9/2010 | Sahatjian | A61F 2/88 623/1.42 |
| 8,476,399 B2 * | 7/2013 | Bolikal | A61L 31/148 528/206 |
| 2006/0233850 A1 | 10/2006 | Michal | |
| 2013/0276669 A1 | 10/2013 | Freier | |
| 2013/0331927 A1 * | 12/2013 | Zheng | A61F 2/82 623/1.19 |

OTHER PUBLICATIONS

Barros, Alexandre A., et al. "Tailor made degradable ureteral stents from natural origin polysaccharides." Tenth Conference on Supercritical Fluids and Their Applications. University of Salerno, 2013.*
Fan, Lihong, et al. "Preparation and characterization of alginate/gelatin blend fibers." Journal of Applied Polymer Science 96.5 (2005): 1625-1629.*
Al-Aown et al. "Ureteral stents: new ideas, new designs." Therapeutic Advances in Urology 2.2 (2010): 85-92.
Association for the Advancement of Medical Instrumentation. "Biological Evaluation of Medical Devices—Part 5: Tests for In Vitro Cytotoxicity" AAMI, 2009. 18 pages.
Augst et al. "Alginate hydrogels as biomaterials." Macromolecular Bioscience 6.8 (2006): 623-633.

(Continued)

*Primary Examiner* — John Pak
*Assistant Examiner* — Daniel L Branson
(74) *Attorney, Agent, or Firm* — Leason Ellis LLP

(57) ABSTRACT

Stents and methods for producing stents are provided. The stent includes a polymeric substrate comprised of 10-50% (w/w) of alginate and 45-85% (w/w) of gelatine and further includes a polymeric biodegradable resin for coating said polymeric substrate. The stent can also include a contrast agent. The stent can further include a crosslinking agent. The method for producing the stent includes dissolving the alginate and gelatine in water and stirring to obtain a polymeric substrate. The method also includes adding a crosslinking agent to the substrate, injecting the substrate into a mold to obtain the stent, placing the stent in a first alcohol solution, and placing the stent in a crosslinking agent solution. The method further includes placing the stent in a second alcohol solution, and a series of interchanging drying and immersing steps.

14 Claims, 16 Drawing Sheets

(56) References Cited

OTHER PUBLICATIONS

Barros et al. "Bioresorbable ureteral stents from natural origin polymers." Journal of Biomedical Materials Research Part B: Applied Biomaterials 103.3 (2015): 608-617.
Blandino et al. "Formation of calcium alginate gel capsules: influence of sodium alginate and CaCl 2 concentration on gelation kinetics." Journal of Bioscience and Bioengineering 88.6 (1999): 686-689.
Chew et al. "Next generation biodegradable ureteral stent in a yucatan pig model." The Journal of Urology 183.2 (2010): 765-771.
Duarte et al. "Unleashing the potential of supercritical fluids for polymer processing in tissue engineering and regenerative medicine." The Journal of Supercritical Fluids 79 (2013): 177-185.
Jejurikar et al. "A novel strategy for preparing mechanically robust ionically cross-linked alginate hydrogels." Biomedical Materials 6.2 (2011): 025010.
Khandwekar et al. "Physicochemical characterisation and biological evaluation of polyvinylpyrrolidone-iodine engineered polyurethane." J. Mater. Sci. Mater. Med., (2011), vol. 22, doi:doi:10.1007/s10856-011-4285-8, pp. 1231-1246, XP019910198.
Krambeck et al. "A novel drug eluting ureteral stent: a prospective, randomized, multicenter clinical trial to evaluate the safety and effectiveness of a ketorolac loaded ureteral stent." The Journal of Urology 183.3 (2010): 1037-1043.
Lange et al. "Ureteral stent-associated complications—Where we are and where we are going." Nature Reviews Urology 12.1 (2015): 17-25.
Liatsikos et al. "Application of paclitaxel-eluting metal mesh stents within the pig ureter: an experimental study." European Urology 51.1 (2007): 217-223.
Lima et al. "Endoscopic closure of transmural bladder wall perforations." European Urology 56.1 (2009): 151-158.
Lingeman et al. "Phase I trial of a temporary ureteral drainage stent." Journal of Endourology 17.3 (2003): 169-171.
Lingeman et al. "Use of a temporary ureteral drainage stent after uncomplicated ureteroscopy: results from a phase II clinical trial." The Journal of Urology 169.5 (2003): 1682-1688.
Lumiaho et al. "A short biodegradable helical spiral ureteric stent provides better antireflux and drainage properties than a double-J stent." Scandinavian Journal of Urology and Nephrology 45.2 (2011): 129-133.
Lumiaho et al. "Drainage and antireflux characteristics of a biodegradable self-reinforced, self-expanding X-ray-positive poly-L, D-lactide spiral partial ureteral stent: an experimental study." Journal of Endourology 21.12 (2007): 1559-1564.
Lumiaho et al. "New bioabsorbable polylactide ureteral stent in the treatment of ureteral lesions: an experimental study." Journal of endourology 13.2 (1999): 107-112.
Lumiaho et al. "The morphological, in situ effects of a self-reinforced bioabsorbable polylactide (SR-PLA 96) ureteric stent; an experimental study." The Journal of Urology 164.4 (2000): 1360-1363.
Mendez-Probst et al. "The use of triclosan eluting stents effectively reduces ureteral stent symptoms: a prospective randomized trial." BJU international 110.5 (2012): 749-754.
Mohanty et al. "Microscopic structure of gelatin coacervates." International Journal of Biological Macromolecules 36.1 (2005): 39-46.
Olweny et al. "Evaluation of the use of a biodegradable ureteral stent after retrograde endopyelotomy in a porcine model." The Journal of Urology 167.5 (2002): 2198-2202.
Schlick et al. "Potentially useful materials for biodegradable ureteric stents." BJU International 80.6 (1997): 908-910.
Taljia et al. "Bioabsorbable SR-PLGA horn stent after antegrade endopyelotomy: a case report." Journal of Endourology 16.5 (2002): 299-302.
Venkatesan et al. "Polymers as ureteral stents." Journal of endourology 24.2 (2010): 191-198.
Zhang et al. "Braided thin-walled biodegradable ureteral stent: Preliminary evaluation in a canine model." International Journal of Urology 21.4 (2014): 401-407.
Zou et al. "A resorbable bicomponent braided ureteral stent with improved mechanical performance." Journal of the Mechanical Behavior of Biomedical Materials 38 (2014): 17-25.
Kong et al. "Controlling rigidity and degradation of alginate hydrogels via molecular weight distribution." Biomacromolecules 5.5 (2004): 1720-1727.

\* cited by examiner

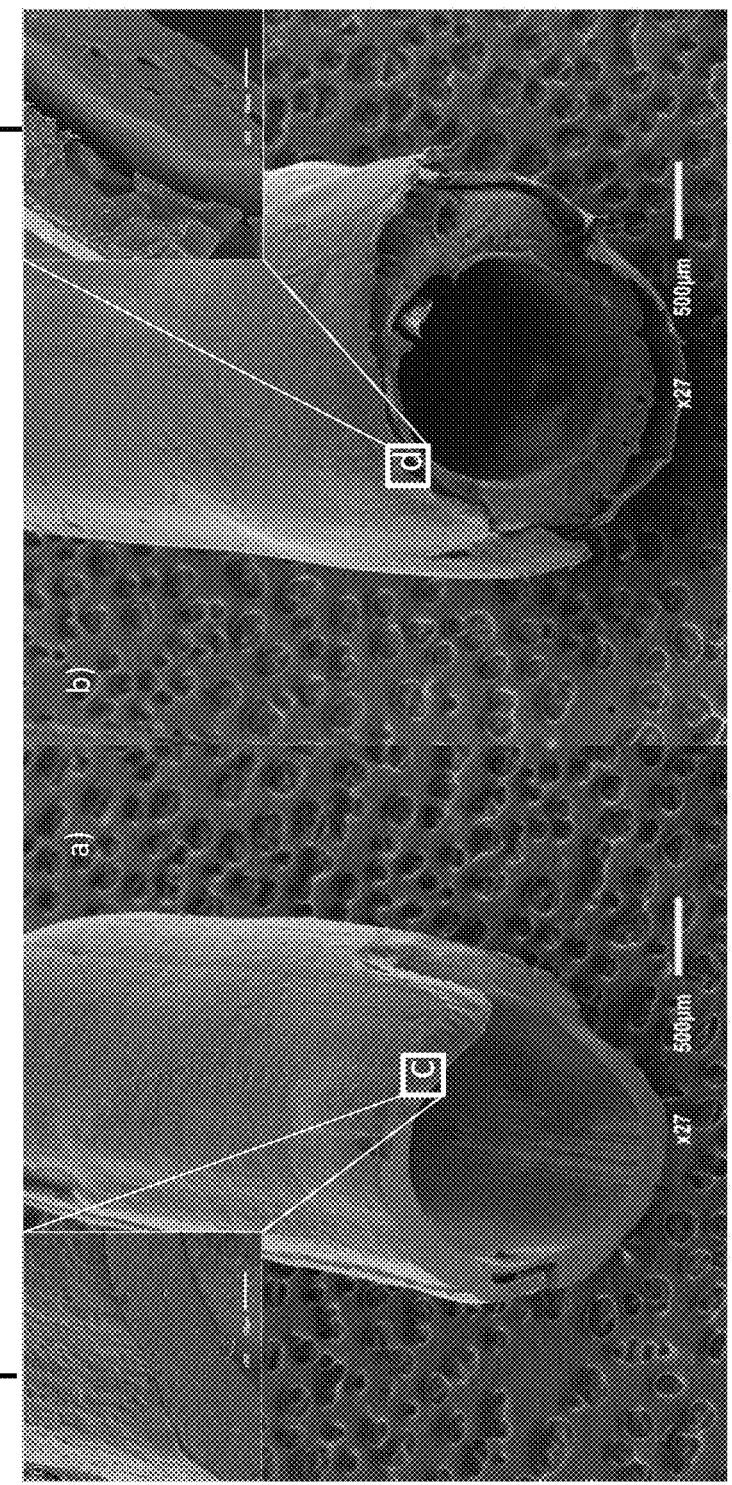

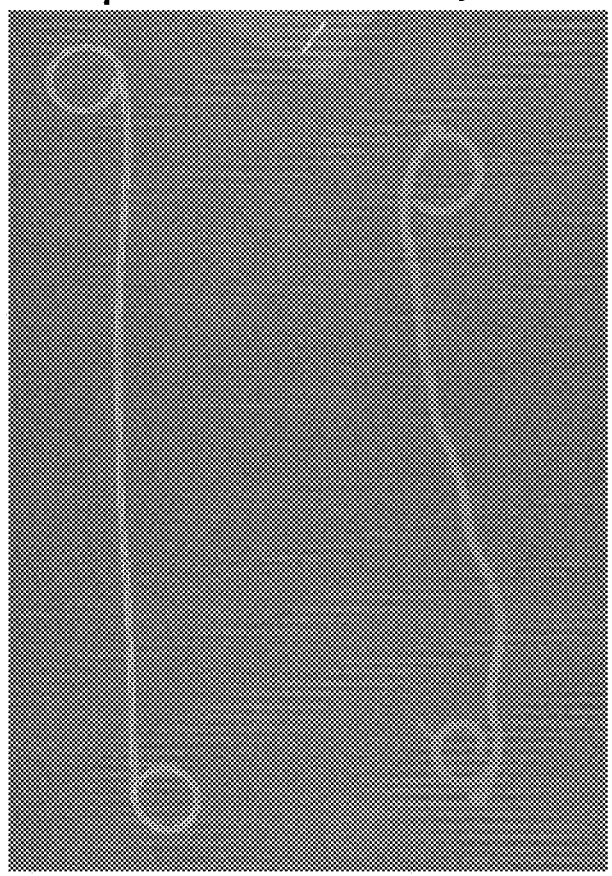

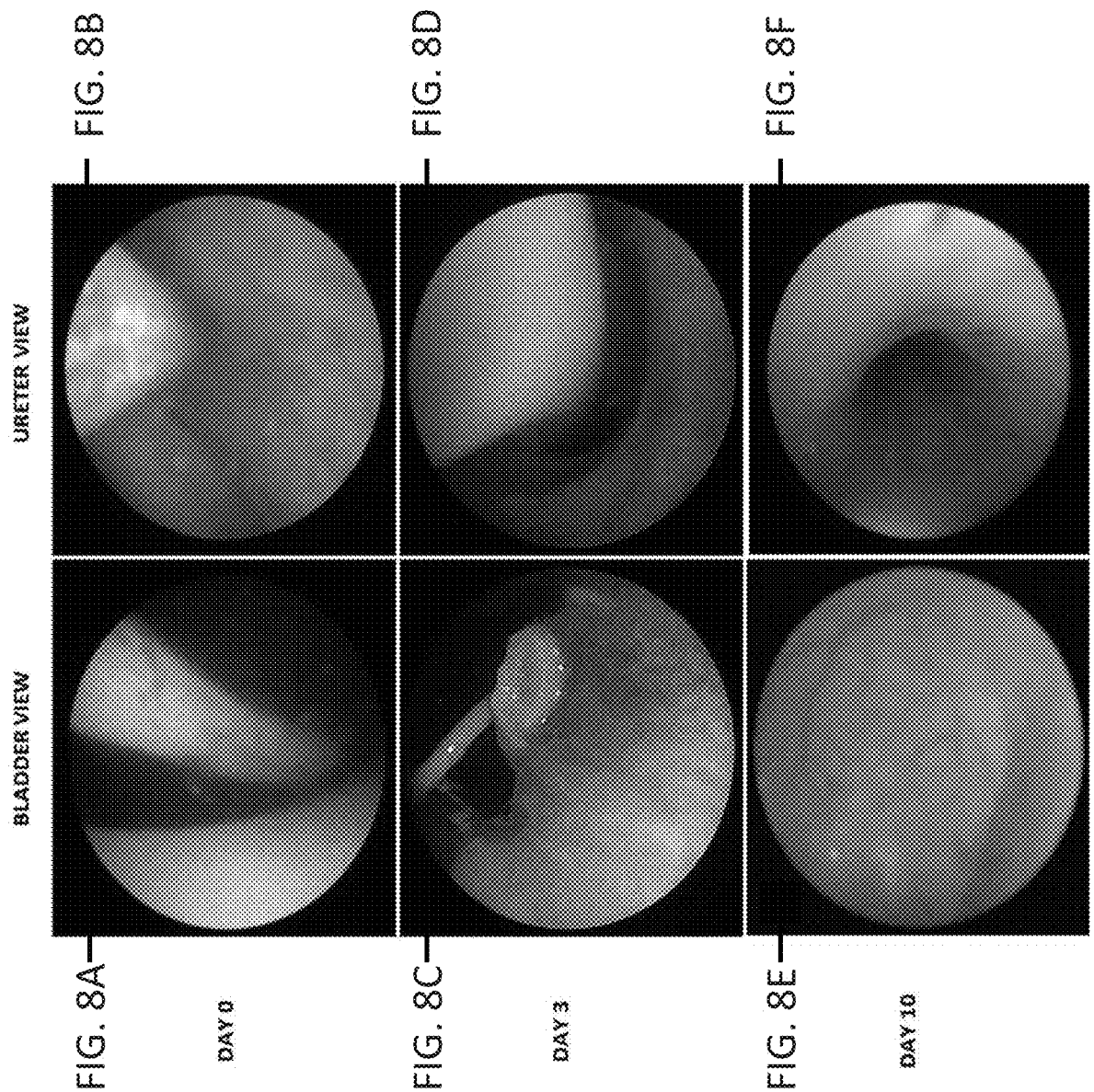

URETERAL STENT, METHODS AND USES THEREOF

CROSS-REFERENCE TO RELATED APPLICATIONS

This application is a U.S. National Stage Application under 35 U.S.C. § 371 of International Patent Application No. PCT/IB2016/052875, filed on May 17, 2016, which claims priority to Portuguese Patent Application No. 108476, filed on May 14, 2015; European Patent Application No. 15169249.8, filed on May 26, 2015; and Portuguese Patent Application No. 109122, filed on Jan. 29, 2016, all of which are hereby incorporated by reference in their respective entireties.

TECHNICAL DOMAIN

The present disclosure relates to ureteral stents, in particular a composition for ureteral stents that are used to ensure patency of a channel, namely the ureter which may be compromised, for example, by a urinary stone, neoplasia or a surgical procedure.

BACKGROUND

A first-generation of biodegradable ureteral stents based on natural origin polymers developed in the state if the art (described in Barros A A, Rita A, Duarte C, Pires R A, Sampaio-Marques B, Ludovico P, Lima E, Mano J F, Reis R L. 2015. Bioresorbable ureteral stents from natural origin polymers; J Biomed Mater Res Part B 2015:103B:608-617) has proven to be an interesting alternative to conventional stents, but it has however demonstrated to fail upon the first in vivo validation in a pig model.

In the first-generation of biodegradable ureteral stents, these were produced using alginate, gellan gum and a blend of these with gelatine (described in Barros A A, Rita A, Duarte C, Pires R A, Sampaio-Marques B, Ludovico P, Lima E, Mano J F, Reis R L. 2015. Bioresorbable ureteral stents from natural origin polymers; J Biomed Mater Res Part B 2015:103B:608-617). The bacterial adhesion of Gram-positive and Gram-negative was assed and compared with a commercial stent (BIOSOFT® duo, Porges, Coloplast) and showed a decrease of adhesion. The biodegradation profile was observed to be highly dependent on the composition of the stent, with a complete dissolution of alginate-based stents during 14 days and the gellan gum-based stents up to 60 days [16]. A first-generation of biodegradable ureteral stents based on natural origin polymers developed previously has proven to be an interesting alternative, but it has however failed upon the first in vivo validation due to its poor mechanical properties (see FIG. 6D).

The most frequent adverse effects reported by patients experiencing ureteral stenting are pain and difficulties in urinary tract [1]. These problems can significantly impact patient quality of life with loss days of working, urinary leakage and sexual difficulties [2]. In last years, new ureteral stent designs have been tested with novel polymers, coatings and the incorporation of active compounds in an attempt to significantly reduce the most common problems like bacterial infection and encrustation [2-4]. Lange et al [1] in a recent review concluded that the stent of the future will be degradable, in a control manner, and possible to coat or elute active compounds. No biodegradable ureteral stent is currently available on the market, although in past year's there has been a crescent interest in this field [1]. Polymers like polylactic acid, polyglycolic acid, poly(lactic-co-glycolic acid) and alginate-based materials have been used to develop the biodegradable ureteral stents [5-9]. Lumiaho, J. et al reported an in vivo studies in pig model using polylactic acid and poly(lactic-co-glycolic acid) based stents which have shown good properties like antireflux properties and favorable drainage but the biocompatibility and the degradation profile were proven to be insufficient for clinical use [5,10,11]. The same ureteral stents showed a different behavior in a canine model, presenting a good biocompatibility and degradation which occurred in 12 weeks [12]. Other studies using poly(lactic-co-glycolic acid)-based ureteral stents reported favorable radiopaque and drainage properties, but the biocompatibility was compromised, according to what is reported in the literature [5,13-15]. The degradation of the ureteral stents must be uniform and homogenous, preventing the formation of fragments during the degradation process that can block the ureter [1,6,16]. URIPRENE® stent (Poly-Med, USA), a radiopaque, glycolic-lactic acid based stent has been designed to degrade in the direction of the bladder coil to renal coil preventing ureteral obstruction secondary to degrading stent fragments [1]. The in vivo pig model studies of URIPRENE® reported a good stability and biocompatibility, with a predictable degradation during 2-4 weeks while maintaining drainage. In previous studies, it was reported an ureteral stent produced with natural based polymers processed by critical point drying with carbon dioxide [16]. This study was however not the first in literature to report alginate-polymer-based temporary ureteral stents. Lingeman et al [9,17] showed in a phase I and phase II clinical trials that these ureteral stents were designed to be intact at least 48 h before degradation with facilitated urinary drainage, favorable tolerability and safety profiles. The problem of these alginate-based stents is the fact that it presented a nonhomogeneous dissolution profile and fragmentation resulting in the need for secondary procedures to remove fragments in some patients.

GENERAL DESCRIPTION

The ureteral stent of the present disclosure overcomes the low mechanical performance encountered in the prior art. Surprisingly a specific concentration of gelatine and alginate as a substrate in conjugation with a polymeric biodegradable resin coating said polymeric substrate, results in stents with higher mechanical properties. This new ureteral stent compositions surprisingly do not fail in the in vivo treatment of mammals (see FIGS. 6D, 7 and 8), and at the same time allows the formation of the new tissue and avoids a second surgical intervention.

In an embodiment, the biodegradable ureteral stents of the present disclosure were coated with a polymeric biodegradable resin. The morphological analysis of the surface of the stents was carried out by scanning electron microscopy. X-ray scan demonstrated the radiocapacity of the biodegradable stents of the present disclosure. The degradation of the biodegradable ureteral stents was assessed in artificial urine solution and it was observed that the degradation of the materials occurs in vitro between 9 and 15 days. Degradation was followed by weight loss of the samples and by chemical analysis of the solutions both by inductive couple plasma (ICP) and gel permeation chromatography (GPC). Formulation with highest amount of gelatine has shown good mechanical performance in terms of tensile properties when compared with the commercial stent (BIOSOFT® duo, Porges, Coloplast), and the crosslinking concentration has shown not to have a great influence on the mechanical behavior of the stents.

In an embodiment, the in vivo performance of ureteral stents of the present disclosure was herein validated. The biodegradable ureteral stents were placed in the ureters of a female pig, following the normal surgical procedure. The animals remained asymptomatic, with normal urine flow, the stents remained intact during the first 3 days and after 10 days the ureteral stents of the present disclosure were totally degraded. This new formulation combined with a new production process overcomes the problems verified with the first-generation of natural based biodegradable stents (described in Barros A A, Rita A, Duarte C, Pires R A, Sampaio-Marques B, Ludovico P, Lima E, Mano J F, Reis R L. 2015. Bioresorbable ureteral stents from natural origin polymers; J Biomed Mater Res Part B 2015:103B:608-617).

The solution now disclosed relates to a composition for biodegradable stents, in particular to ureteral stents. This disclosure overcomes the problems encountered in the available stents, in particular, ureteral stents, as it namely:
avoids the need for a second surgery for stent removal;
decreases the morbidity in patients submitted to a surgical procedure;
decreases or eliminates the risk of infection after the implantation of the ureteral stent.

The problems mentioned in the prior art are surprisingly solved by the composition of the present subject matter that provides a stent:
that is not rejected by the mammal body,
this stent has improved mechanical properties and allows the implantation of the device in vivo in the mammal animal model,
eliminated by the mammal patient submitted to a surgical procedure, and
that is in the organism enough time to recover from the surgical procedure performed.

Furthermore, composition of the present subject matter may further comprise active/therapeutic agent for local release, in particular anti-inflammatory, anti-microbial, an anti-cancer agent, or mixtures thereof. Surprisingly results were achieved were the therapeutic drug is incorporated in the polymeric subtract.

The present disclosure relates, in particular to a new composition and to a new method of injection moulding and drying to fabricate the stents, in particular ureteral stents. Additionally, the degradable ureteral stents were coated with a biodegradable polymer. In particular, this disclosure makes the degradable ureteral stents made by origin polymers a success in vivo, four formulations with different concentrations of gelatine and alginate and different concentrations of crosslink agent were tested in order to obtain higher mechanical properties.

The composition of the present subject matter is degradable by the organism of the mammal and the combination with the method of obtain said stent avoids the obstruction of the stent by itself when in contact with a fluid, namely in the mammal organism.

The present disclosure relates to a stent, namely an ureteral stent, comprising a polymeric substrate wherein the polymeric substrate comprises 10-50% (w/w) of alginate and 45-85% (w/w) of gelatine; and a polymeric biodegradable resin for coating said polymeric substrate.

In an embodiment, for better results, the polymeric substrate may comprise 20-40% (w/w) of alginate and 55-70% (w/w) of gelatine.

In an embodiment, for better results, a solution of 3-50% (w/v) of resin is added to said stent; preferably a solution of 5-20% (w/v) of resin is added to said stent, more preferably a solution of 5-10% (w/v) of resin is added to said stent.

In an embodiment, for better results, the stent may further comprise a contrast agent, namely an X-ray contrast agent. In an embodiment, bismuth was added to confer radiopaque properties to the stent.

In an embodiment, for better results, the stent now disclosed may comprise:
2-5% (w/w) of the contrast agent, preferably 5% (w/w) of the contrast agent, namely bismuth (III) carbonate;
the polymeric substrate may comprise 20-40% (w/w) of alginate and 55-70% (w/w) of gelatine, preferably the polymeric substrate may comprise 30% (w/w) of alginate and 65% (w/w) of gelatine.

In an embodiment, for better results, the polymeric biodegradable resin for coating the polymeric substrate may be selected from the following list: polycaprolactone resin, polyglycolide and its copolymers: poly(lactic-co-glycolic acid with lactic acid), poly(glycolide-co-caprolactone) with ε-caprolactone, and poly (glycolide-co-trimethylene carbonate) with trimethylene carbonate, or mixtures thereof.

In an embodiment, for better results, the contrast agent may be selected from the following list: barium salts, bismuth salts, spinel pigments, or mixtures thereof, in particular bismuth (Ill) carbonate.

In an embodiment, for better results, the stent may further comprise a crosslinking agent, wherein said crosslinking agent is a chemical crosslinker comprising a functional group able to react with gelatine amines, preferably the crosslinking agent is selected from the following list: ionic crosslinking agents include monovalent or divalent ions, from which the cation is calcium, magnesium, barium, strontium, boron, beryllium, aluminium, iron, copper, cobalt, lead or silver; the anion is selected from the group consisting of chloride, nitrate, phosphate, citrate, borate, succinate, maleate or oxalate, or mixtures thereof.

In an embodiment, for better results, the crosslinking agent may be select from a group consisting of calcium chloride, genipin, glutaraldeyhyde, carbodiimides, and mixtures thereof.

In an embodiment, for better results, the stent may further comprise a therapeutic agent namely an anti-inflammatory agent, an anti-microbial agent, an anti-cancer agent, an antiviral agent, or mixtures thereof.

In an embodiment, for better results, the stent may further comprise an anti-inflammatory agent selected from the following list: prednisolone, methylprednisolone, fluorometholone, dexamethasone, betamethasone, hydrocortisone, medrysone, loteprednol, rimexolone, triamcinolone, diclofenac, ketorolac, flurbiprofen, indomethacin, suprofen, ibuprofen, ketorolac tromethamine, emedastine, levocabastine, azelastine, olopatadine, ketotifen, ketoprofen, cromolyn, iodoxamide or mixtures thereof.

In an embodiment, for better results, the stent may further comprise an anti-microbial agent selected from the following list: amoxicillin, dicloxacillin, augmentin, cephalosporins, gentamycin, tobramycin, neomycin, erythromycin, azithromycin, clarithromycin, ofloxacin, ciprofloxacin, norfloxacin, levofloxacin or mixtures thereof.

In an embodiment, for better results, the stent may further an anti-cancer agent selected from the following list: methotrexate, vinblastine, doxorubicin, cisplatin, granulocyte colony-stimulating factor, gemcitabine, carboplatin, 5-fluorouracil ifosfamide, pemetrexed, paclitaxel, epirubicin, mitomycin C, capecitabine, *Bacillus* Calmette-Guerin (BCG) or mixtures thereof.

In an embodiment, for better results, the stent may further comprise an antiviral agent selected from the following list: acyclovir, valacyclovir, famciclovir or mixtures thereof.

In an embodiment, for better results, the therapeutic agent may be incorporated in the polymeric substrate.

In an embodiment, for better results, the therapeutic agent may be incorporated in the coating of the polymeric substrate.

In an embodiment, for better results, the stent now may be for use in human or veterinary medicine, in particular the stent may be for use in regenerative medicine or tissue engineering.

In an embodiment, for better results, the stent may be for use in the prevention or treatment of urologist diseases.

In an embodiment, for better results, stent now disclosed may be an ureteral stent.

The present disclosure also relates to a method for producing of a stent, in particular an ureteral stent, comprising the following steps:
- dissolving alginate, gelatine and in water at 40-90° C., preferably 70° C.; stirring at 300-1500 rpm, for 30 minutes-3 hours, preferably at 600 rpm and for 1 hour to obtain a polymeric substrate;
- optionally adding a chemical crosslinker to the polymeric substrate;
- injecting the polymer substrate in a mould to obtain a stent;
- placing the stent in an alcohol solution for 30 minutes-3 hours, preferably for 1 hour;
- placing the stent in a 0.05-2 M crosslinking agent solution under constant stirring for 1-24 hours, preferably for 2 hours, at 20-25° C.;
- placing the stent in an alcohol solution;
- drying the stent in a high-pressure vessel with a supercritical fluid, in particular carbon dioxide, at 35-60° C., 71-200 bar and 60-360 minutes, in continuous mode;
- immersing the stent in water for 15-90 minutes, preferably 30 minutes;
- immersing the stent in ethanol for 1-5 hours, preferably for 1 hour;
- drying the stent 20-25° C. for 1 day;
- immersing the stent in a solution of 5-20% resin, preferably 10% of polycaprolactone for 5-30 seconds, preferably 10 seconds;
- drying at 15-35° C., preferably 20° C. and for 12-24 hours, preferably for 15 hours.

In an embodiment, for better results, the step of dissolving alginate and gelatine may further comprise dissolving bismuth (III) carbonate.

In an embodiment, for better results, the step of adding the crosslinking agent may be made by supercritical fluid impregnation at 35-50° C., 100 bar and for 2 hours or by addition of the therapeutic agent to the polymeric substrate.

In an embodiment, for better results, the concentration of the crosslinking agent, preferably an ionic crosslink agent, may be between 5-50 mM, preferably 5-20 mM.

In an embodiment, for better results the concentration of the crosslinking agent solution may be 0.24 M, 0.48 M, 1M.

In an embodiment, for better results, the drying step in the high-pressure vessel with carbon dioxide may be carried out at 40° C., 100 bar and 90 minutes.

The present disclosure also relates to a composition for use in a method of preventing or treating urologist diseases comprising alginate, gelatine and a polymeric biodegradable resin,
- wherein said composition is administrated in a biodegradable stent,
- wherein said stent comprises 10-50% (w/w) of alginate and 45-85% (w/w) of gelatine, as a substrate, and the polymeric biodegradable resin as a substrate coating.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

BRIEF DESCRIPTION OF THE DRAWINGS

The following figures provide preferred embodiments for the present disclosure and should not be seen as limiting the scope of the disclosure.

FIGS. 1A-1D. SEM micrographs of the biodegradable ureteral stent (6 Fr, formulation 2, 0.48M) before coating (FIG. 1A), after coating (FIG. 1B), higher magnificence of one layer hydrogel (FIG. 1C), and higher magnificence of two layers coating and hydrogel (FIG. 1D).

FIGS. 2A-2B. Radiograph in abdomen mode of commercial ureteral stent (BIOSOFT® duo, Porges, Coloplast) (FIG. 2A) and biodegradable ureteral stent developed (formulation 2, 0.48M) (FIG. 2B).

FIG. 3A: Different formulations tests; and FIG. 3B: Formulation 2 with different crosslinking concentration.

FIG. 6D provides images of biodegradable stents before and after coating in dry state and in wet state immersion in AUS (scale bar 2 mm). ctr—(BIOSOFT® duo, Porges, Coloplast). Values are represented as average±SD, n=3. Statistical differences (*$p<0.05$, **$p<0.01$) using one way-ANOVA followed by a Tukey post-test.

FIGS. 8A-8F. Conventional ureteroscopy of the stented ureter in vivo in a pig model: biodegradable ureteral stent placement (FIG. 8A); biodegradable ureteral stent inside the right ostium pig ureter at placement time (FIG. 8B); biodegradable ureteral stent after 3 days at the entrance of the right ostium pig ureter (FIG. 8C); after 3 days with the biodegradable ureteral stent (FIG. 8D); after 10 days of the biodegradable ureteral stent (FIG. 8E); and right ostium pig ureter after the degradation at day 10 (FIG. 8F).

MATERIALS AND METHODS

Figure 3A:
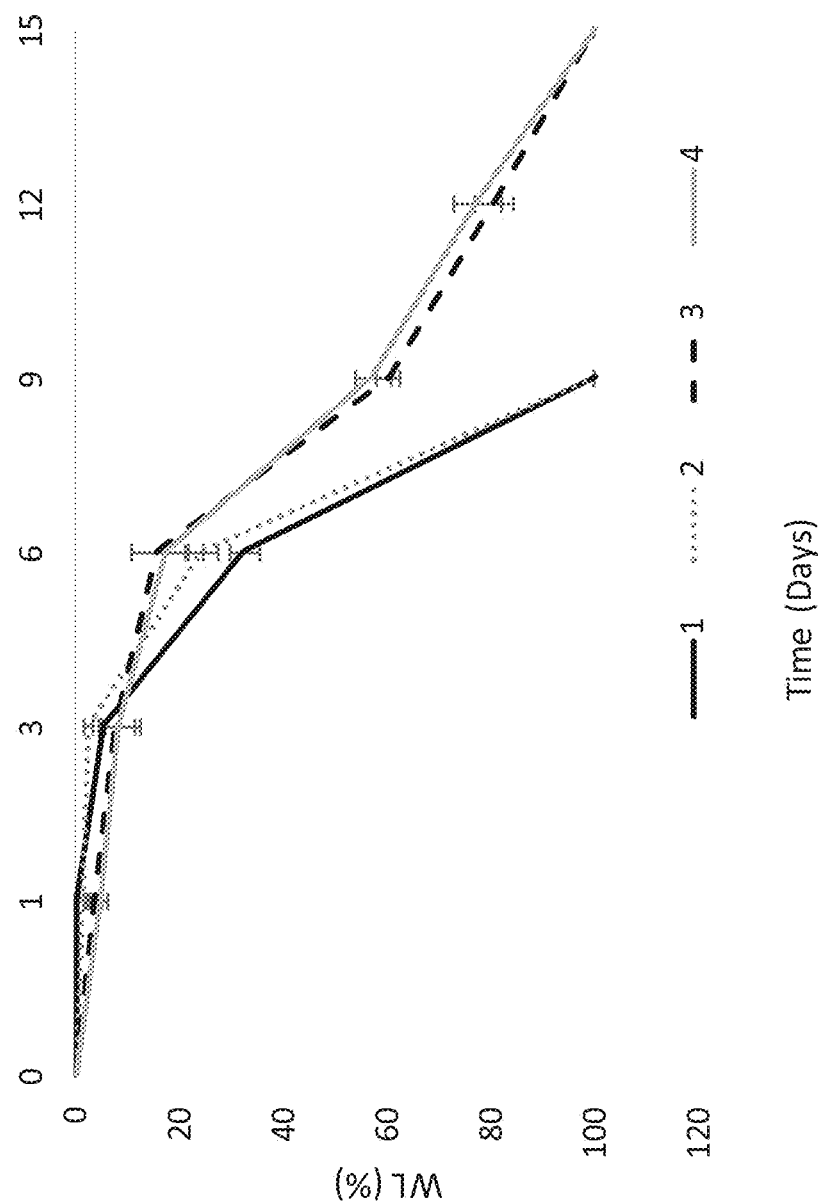
FIGS. 3A-3B. Weight loss of developed biodegradable ureteral stents.

Materials—In an embodiment, alginic acid sodium salt, gelatin, urea, urease type IX from *Canavalia ensiformis* (Jack Bean), calcium chloride, chlorophorm, ethanol, bismuth (III) carbonate basic, sodium phosphate dibasic and sodium azide were purchased from Sigma-Aldrich (Germany). Potassium dihydrogen ortho-phosphate and magnesium chloride hexahydrate were obtained from Riedel-de Haen (Germany).

Bismuth standard for ICP was obtained from Sigma-Aldrich (Germany). Polycaprolactone resin PCL 787, commercially available as TONE™ polymer, was obtained from Union Carbide Chemicals and Plastics Division, Bound Brook, N.J. Carbon dioxide (99.998 mol %) was supplied by Air Liquide (Portugal). All reagents were used as received without any further purification.

Preparation of second generation of biodegradable ureteral stents—In an embodiment, Polymers were dissolved in hot distilled water (70° C.) at different concentrations as described in table 1. The solutions were stirred for 1 hour and the polymeric solution was injected in a mold to obtain a tubular structure. After 1 hour the piece was taken out of the mold and placed in an alcohol solution (100% ethanol) for 1 hour. The stents were then transferred into a cross-linking solution of calcium chloride ($CaCl_2$), with different concentrations (table 1) at room temperature. After cross-linking, the stents were relocated in an alcoholic solution (100% ethanol) to obtain an alcohol gel which can be dried in a high-pressure vessel with supercritical carbon dioxide ($scCO_2$) under controlled pressure (100 bar) and temperature (40° C.) and a continuous flow of the $scCO_2$ during 90 minutes. Finally, the dried stents were immersed in distilled water for 30 min and in ethanol 100%, for 1 hour, to remove the template. The stents were finally dried at room temperature conditions, during 1 day. The coating of the stents was performed by immersion in a 10% of polycaprolactone (PCL) resin 787 dissolved in chloroform. The stents were dried at ambient conditions overnight. Commercial BIOSOFT® duo, Porges, Coloplast used as a control in this study is also shown.

TABLE 1

Summary of the formulations tested to prepare the different biodegradable ureteral stents.

| Formulation | Material conc. (wt. %) | | | | Crosslinking agent | Crosslinking agent conc. (M) |
|---|---|---|---|---|---|---|
| | 1 | 2 | 3 | 4 | | |
| Alginate | 10 | 30 | 45 | 50 | $CaCl_2$ | 0.24 |
| Gelatine | 85 | 65 | 50 | 45 | | 0.48 |
| Bismuth (III) carbonate basic | 5 | 5 | 5 | 5 | | 1 |
| Coating | | | | | | 10% PCL resin PCL 787 |

Scanning electron microscopy—In an embodiment, the morphology of the biodegradable stents was analyzed on a JEOL SEM, model JSM-6010LV. The samples were fixed with mutual conductive adhesive tape on aluminum stubs and covered with gold/palladium using a sputter coater.

Postoperative X-ray—In an embodiment, the radiopaque characteristics of the biodegradable ureteral stent developed were evaluated in a postoperative X-ray equipment located at the Department of Imaging Hospital de Braga, Portugal. The radiographs were taken in abdomen mode with magnification of 0.27×.

Degradation Study—In an embodiment, the degradation of biodegradable stents was measured as function of the weight loss of the samples. Samples (10 mg) were immersed in artificial urine solution (AUS) prepared according Khandwekar et al [18] with the composition presented in table 2. Samples immersed were dried and weighted to determine the weight loss, which was calculated according to the following equation:

$$\% \text{ Weight loss} = (W_f - W_i)/W_i * 100 \quad (1)$$

Where $W_f$ is the final weight of the sample (dried after immersion) and $W_i$ is the initial weight of the sample. Each formulation was tested in triplicate.

TABLE 2

Composition of the artificial urine solution (AUS).

| | Component | % wt/v |
|---|---|---|
| Solution A | Potassium dihydrogen ortho-phosphate | 0.76 |
| | Magnesium chloride hexahydrate | 0.36 |
| | Urea | 1.60 |
| Solution B | Calcium chloride hexahydratate | 0.53 |
| | Chicken ovalbumin | 0.2 |
| Urease type IX from *Canavalia ensiformis* (Jack Bean) | | 0.125 |

Gel permeation chromatography (GPC)—In an embodiment, 5 mg of alginate, gelatine and bismuth were dissolved in 5 ml of an aqueous solution of sodium phosphate dibasic 0.01 M containing 0.1 M of sodium azide (pH 6.6) and used as a controls, while the immersion solutions obtained by degradation test of stents formulation 2 at specific time point (1, 3, 6 and 9 days) were lyophilized and then dissolved in 5 ml of the same eluent. The solutions were filtered through a 0.221 μm filter and analyzed on a gel permeation chromatograph (Malvern, Viscotek TDA 305) with refractometer, right angle light scattering and viscometer detectors on a set of four columns: pre-column Suprema 5 μm 8×50 S/N 3111265, Suprema 30 Å 5 μm 8×300 S/N 3112751, Suprema 1000 Å 5 μm 8×300 S/N 3112851 PL and Aquagel-OH MIXED 8 μm 7.5×300 S/N 8M-AOHMIX-46-51, with refractive index detection (RI-Detector 8110, Bischoff). Elution was performed at 30° C. using a flow rate of 1 ml min-1. The elution times and the RI detector signal were calibrated with a commercial calibration polysaccharide set from Varian that contains 10 Pullulan calibrants with narrow polydispersity and Mp (molecular mass at the peak maximum) ranging from 180 Da to 708 kDa.

Inductive coupled plasma (ICP)—In an embodiment, the immersion solutions from the degradation test of the stents, formulation 2, were filtered and analyzed by inductive coupled plasma (ICP) to follow Bismuth (BI) concentration during the different degradation times. The sample absorption at specific wavelengths (k=206.17 nm for Bi) was measured, and the bismuth concentration was determined using a calibration curves previously obtained with Bismuth standard for ICP (Sigma) ($R^2$=0.96).

Cytotoxicity evaluation of the leachables—In an embodiment, the cytotoxicity of the leachable materials during the ureteral stent degradation in AUS was accessed according to ISO/10993 [19]. The cytotoxicity of the samples was assessed using an immortalized mouse lung fibroblasts cell line (L929) purchased from the European Collection of Cell Cultures. First, the immersion solutions obtained by degradation test at specific time point (1, 3, 6 and 9 days) of stents formulation 2 were lyophilized. The leachables were dissolved in basal medium DMEM (Dulbecco's modified Eagle's medium; Sigma-Aldrich, Germany) 10% FBS (heat-inactivated fetal bovine serum, Biochrom AG, Germany), and 1% antibiotic-antimycotic (Gibco, UK). Cells were cultured in a humidified incubator at 37 C in a 5% $CO_2$ atmosphere. The effect of the leachables on the cellular metabolism was performed using a standard MTS (CELL-TITER 96® Aqueous Solution Cell Proliferation Assay, Promega, USA) viability test. A latex rubber extract was used as positive control for cell death; while cell culture medium was used as negative control representing the ideal situation for cell proliferation. Cell viability was evaluated by the MTS assay after 72 h. This was quantified by UV-spectroscopy, reading the formazan absorbance at 490 nm in a microplate reader (Synergy HT, Bio-Tek Instruments, USA). Each sample formulation and control were tested using 12 replicates.

Tensile mechanical analysis—In an embodiment, the Tensile mechanical analysis of the biodegradable stents was evaluated using an INSTRON 5540 (Instron Int. Ltd, High Wycombe, UK) universal testing machine with a load cell of 1 kN. The wet samples were hydrated before testing in AUS for 4 hours. The dimensions of the specimens used were 5 mm of length, 2 mm width, and 0.5 mm of thickness. The load was placed midway between the supports with a span (L) of 3 mm. The crosshead speed was 1:5 mm min-1. For each condition the specimens were loaded until core break. The results presented are the average of at least three specimens and the results are presented as the average±standard deviation.

Surgical procedure and in vivo degradation validation—In an embodiment, the preliminary in vivo validation study was conducted at Minho University, Braga, Portugal, after formal approval by the institution's review board and in accordance with its internal ethical protocol for animal experiments. Female domestic pigs, weighing=30 kg, was used to validate the procedure and the stent degradation. The pigs were not given food or water for 12 h before the procedure. All procedures were performed under general anesthesia and mechanical ventilation as previously described in detail [20]. After emptying the bladder, a semi rigid 7 Fr ureteroscope (Karl Storz, Tuttlingen, Germany) was inserted through the urethra and it was instilled serum. The full procedure was according the standard technique of ureteroscopy. A 0.035-inch flexible tip guidewire (AQUA-TRACK® Hydrophilic Nitinol, Cordis®, Johnson & Johnson) was then inserted in the ureters. The biodegradable ureteral stents were guided by the guidewire until placed in either the right and left ureter, one at time. Finally, a conventional ureteroscopy was performed in order to verify the degradation and the presence of any fragment and the morphology of the ureters.

Statistical analysis. In an embodiment, all data values are presented as mean±standard deviation (SD). Statistical analysis was performed using Graph Pad Prism 6.00 software (San Diego, USA). Statistical significances (*$p<0.05$, $p<0.01$ and *$p<0.001$) were determined using one-way analysis of variance (ANOVA) for an average of three to twelve replicates, followed by post hoc Tukey's test for all pair-wise mean comparisons.

To prepare the second-generation of biodegradable ureteral stents made by origin polymers new formulations were tested and the method of injection moulding and drying was optimized. The idea to coat the hydrogel with another biodegradable material with the objective to enhance the stent mechanical properties was also tested with a poly-caprolactone resin PCL 787. Polycaprolactone resin was chosen as it is a safe material and has a fast degradation in comparison with other biodegradable polymers. The biodegradable ureteral stents are prepared from an initial aqueous solution of alginate-gelatine from which gelation is induced by decreasing the temperature followed by an ionic cross-linking with a $CaCl_2$ solution. Gelatine and alginate were chosen because of their versatility to form gels and the results obtained in the previous study [16] combining gelatine with other polysaccharides it is possible to induce changes in the water uptake, degradation profile and particularly were benefices regarding bacteria adhesion. In this disclosure bismuth was added to the formulation. The use of bismuth in the new formulation provides radiopaque properties to the ureteral stent due the inherent radiopaque characteristics of this compound. This material was already used and prove to be safe and it is already FDA approved [21]. After crosslinking a combination of steps in ethanol and supercritical carbon dioxide were further employed to dry the biodegradable ureteral stents. Supercritical drying process parameters were kept as in the first version of this stents as they had already been optimized supercritical fluid drying process used is a process in which the matrices do not undergo any phase transition and therefore the integrity of the lumen of the stents is not compromised [22]. Different other drying methods were tested namely air drying but the integrity of the lumen of the stents was compromised, unlike what was observed when using supercritical fluid $CO_2$.

Morphology. FIGS. 1A-1D present the SEM images of the cross-sections of biodegradable ureteral stent developed according to the formulation 2. In FIG. 1A the uncoated stent is shown and in FIG. 1B the stent with PCL coating. FIGS. 1C and 1D are the magnifications of stent wall. It is possible to distinguish the two layers, outer layer from PCL coating and the inner layer the alginate-gelatine plus bismuth matrix. The inner diameter, i.e. the lumen of the stent is 2 mm. The inner and outer diameter and the length of the stents are only dependent on the injection mold used to prepare them, and do not depend on the formulation tested. Like in the first-generation of the biodegradable ureteral stents the surface obtained without coating is similar [16].

X-Ray validation. An important feature of the ureteral stents is its radiopacicity. The possibility to assess by postoperative X-ray, localize the stent in the body and follow the degradation during time is of major importance and for this it is used a standardized product, namely bismuth (III) carbonate basic, however, others can be used. In FIGS. 2A-2B is possible confirm the radiopacity, in wet state, of the biodegradable ureteral stent developed (FIG. 2B) in comparison with commercial stent (FIG. 2A). In this disclosure, a lower concentration of this compound in the formulation was used, as compared to the Lingeman et al [21], demonstrating unexpected that low amounts are suitable to provide this feature to the stent.

Figure 3B:
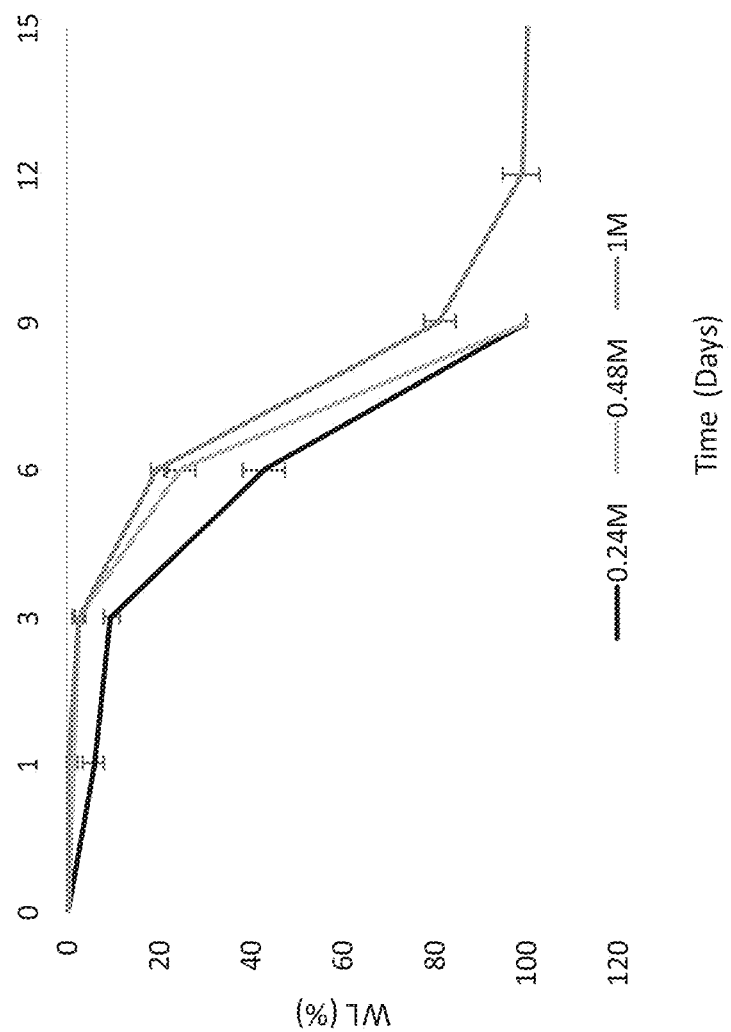

In vitro degradation study—The in vitro degradation of the biodegradable ureteral stents with the different formulations and different concentrations of crosslinking agent was assessed measuring the weight loss of the samples. The weight loss, measured as the percentage of mass lost when immersed in AUS for a predetermined time period is presented in FIGS. 3A-3B. All the conditions tested demonstrated in vitro that no degradation occurs during the first 3 days of immersion. After 9 days the stents have shown complete degradation. Comparing the different formulations tested, the results suggest that higher concentration of alginate (formulations 4 and 5, FIG. 3A) increase the degradation time. Comparing the different concentrations of crosslinking agent (FIG. 3B) the results show that stronger cross-linking lower is the degradation even thought not statistically significant. This can be justified due to the presence of more calcium crosslinks with guluronic acid (G) blocks, increasing their covalently cross linked network [23]. The divalent cations of the ionic crosslinking agent, bind exclusively to the G-blocks of the adjacent alginate chains, since the structure of the L-guluronate offers a greater flexibility than the D-mannuronate chains. By creating ionic inter-chain bridges, divalent ions replace the hydrogen bonds between the carboxyl group of D-mannuronate and the 2-OH and 3-OH groups of the subsequent L-guluronate, originating the gelation of aqueous alginate solutions [24,25]. The G-block length, concentration of polymer and molecular weight are thus critical factors affecting the physical properties of alginate and its resultant degradation. In the other hand, gelatine can form hydrogels by increasing and decreasing temperature, which is merely a physical crosslinking phenomena. The mechanism behind the crosslinking of gelatine molecules is a conformational change from a random coil to a triple helix. The degradation occurs then because the noncovalent associations are easily disrupted at temperatures higher than 30-35° C., therefore at body temperature [26]. This helps to understand that with higher amounts of gelatine in the formulation a faster degradation will take place. In our previous study, the alginate-based ureteral stents showed a slower degradation comparing with this work, for the same reason [16]. The polymer blend with the alginate is however unknown and hence difficult to establish a work correlation compared with formulation now disclosed.

Figure 4:
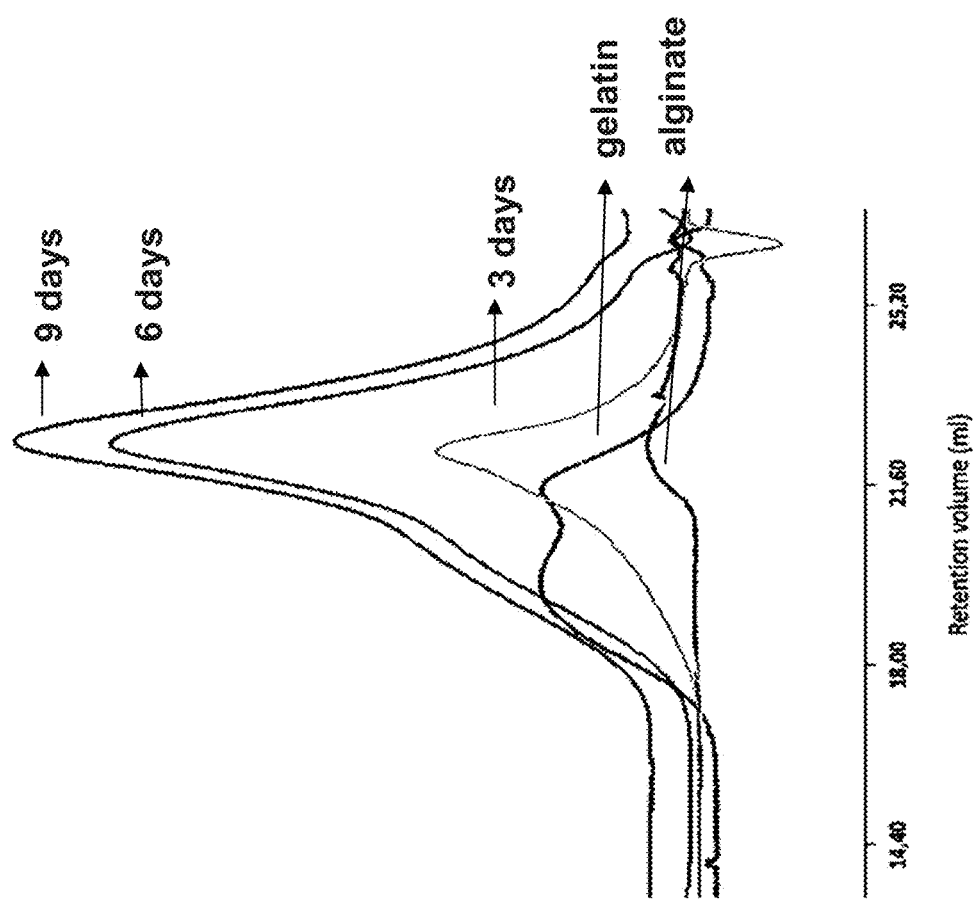
FIG. 4. GPC chromatograms of stent raw materials (alginate and gelatin) and the leachables at 1, 3, 6 and 9 days' time points.

Gel permeation chromatography (GPC)—The polymeric extractables from the ureteral stent degradation at 1, 3, 6 and 9 days were first lyophilized and then dissolved in an appropriate eluent to be analyzed by GPC. As a control the raw materials alginate and gelatine were injected. GPC pattern of alginate and gelatine show an overlap of the eluting peaks between 18 ml and 21 ml of retention volume hence it is not easy to distinguish both (FIG. 4). The extractables are composed essentially by the mixture of alginate and gelatine present in the biodegradable ureteral stent formulation. The overlap of the raw materials makes it difficult to identified separately the presence of the alginate and gelatin. However, it is possible see the peaks of the elution curve with increasing intensity with the degradation time. Considering the retention volume of the peaks on the different elution curves, it is observe a major contribution of gelatine instead of alginate. This was expected because this formulation (formulation 2) is composed of 65% gelatine and 30% alginate.

Inductive Couple Plasma (ICP)—The ICP analysis of bismuth concentration in the immersions solutions from different time points from formulation 2 is present in table 3. The results show a gradual release of bismuth during the degradation process from the stent to the artificial urine solution. According to the degradation profile (FIG. 3A) of ureteral stents, formulation 2, and the bismuth measured in the immersion solutions, it is shown that the release of bismuth is associated with the degradation and it does not occurs due to swelling of the stent or diffusion from the stent to the AUS. To support this observation and considering a homogenous distribution of bismuth in the stent, it would be expected to have a correlation between the degradation profile and the amount of bismuth in solution. At day 3 the ureteral stent with formulation 2 presents a degradation around 5%, corresponding the value of bismuth in solution is 0.271 g/L, that is approximately 5% of the total bismuth present in the stent. The same is observed at time point day 6 in which the value 1.285 g/L is 20% of the total bismuth and again is close to the value of the degradation observed in FIG. 3A.

TABLE 3

Concentration of bismuth obtained by ICP, in immersion solution (AUS) during the degradation.

| Days | Bismuth (g/L) | Std | Release (%) |
|---|---|---|---|
| 1 | 0.0570 | 0.0058 | ~1% |
| 3 | 0.271 | 0.0496 | ~5% |
| 6 | 1.285 | 0.06 | ~20% |
| 9 | 5.953 | 0.1912 | 100% |

Figure 5:
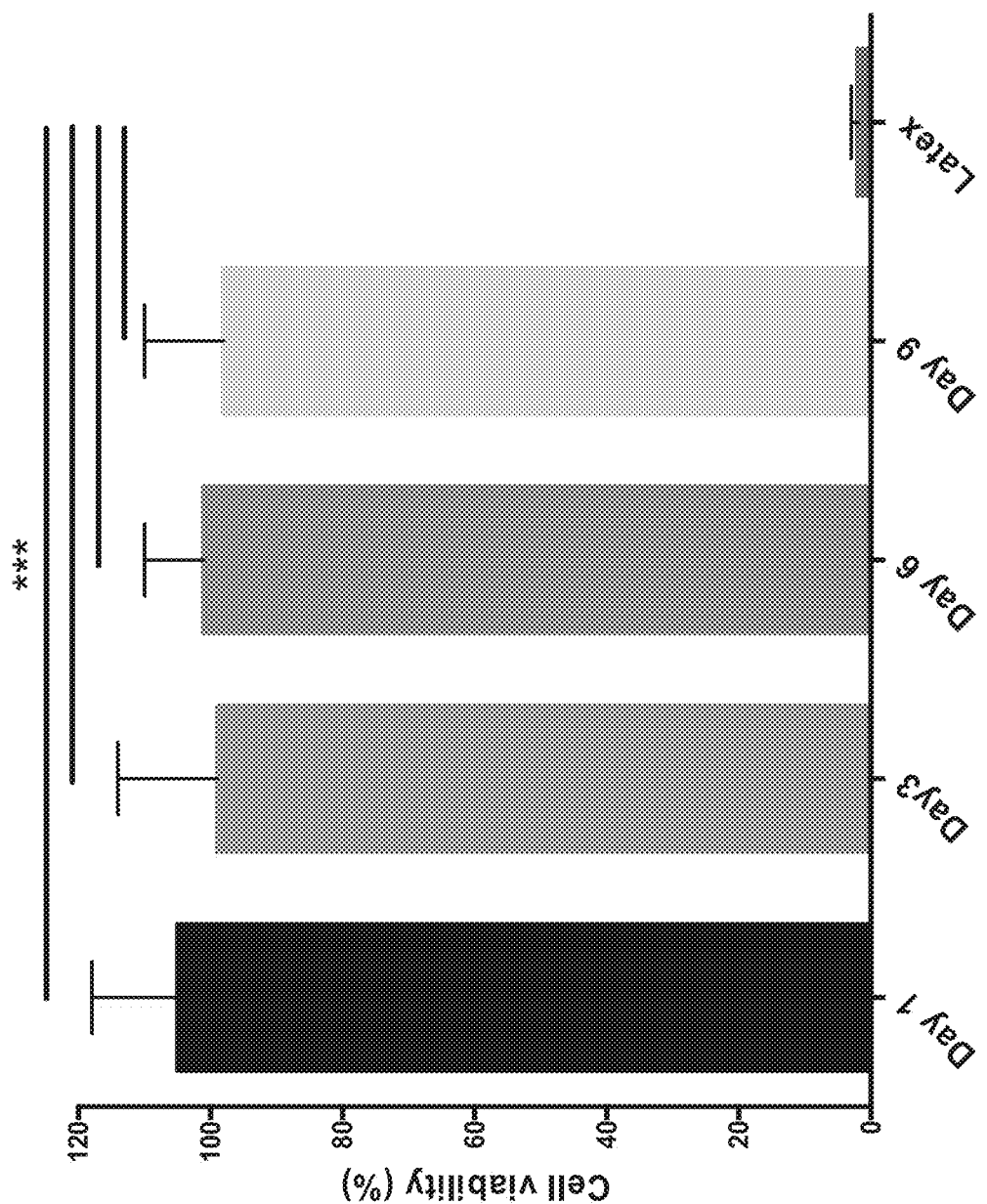
FIG. 5. Cytotoxicity study by cell viability measured after 72 h.
Figure 6A:
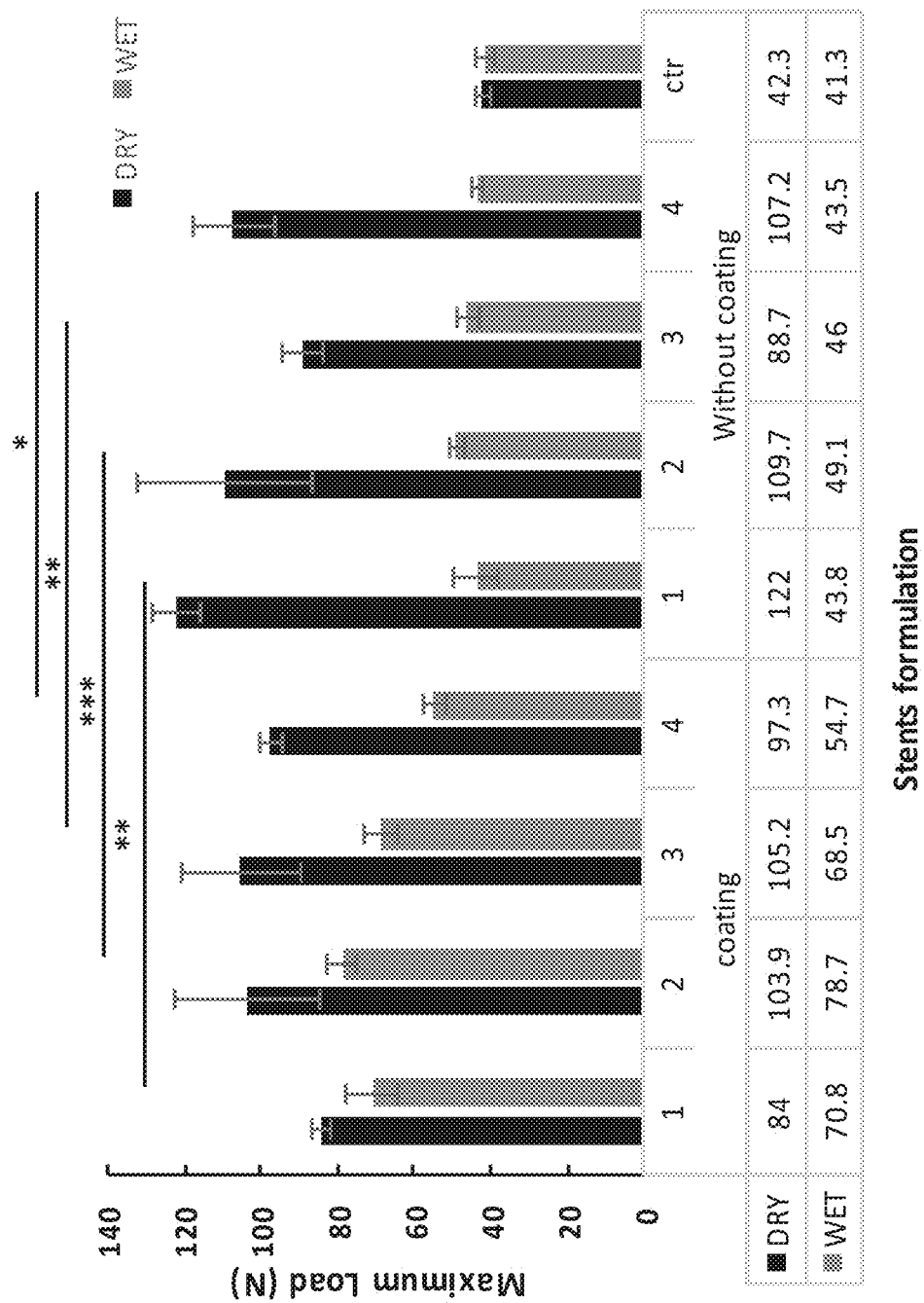
FIGS. 6A-6D. Mechanical properties of the biodegradable stents (0.48M crosslinking concentration) before and after PCL coating in terms of maximum load (N) (FIG. 6A), maximum tensile strain (%) (FIG. 6B), and young modulus (MPa) (FIG. 6C).
Figure 6B:
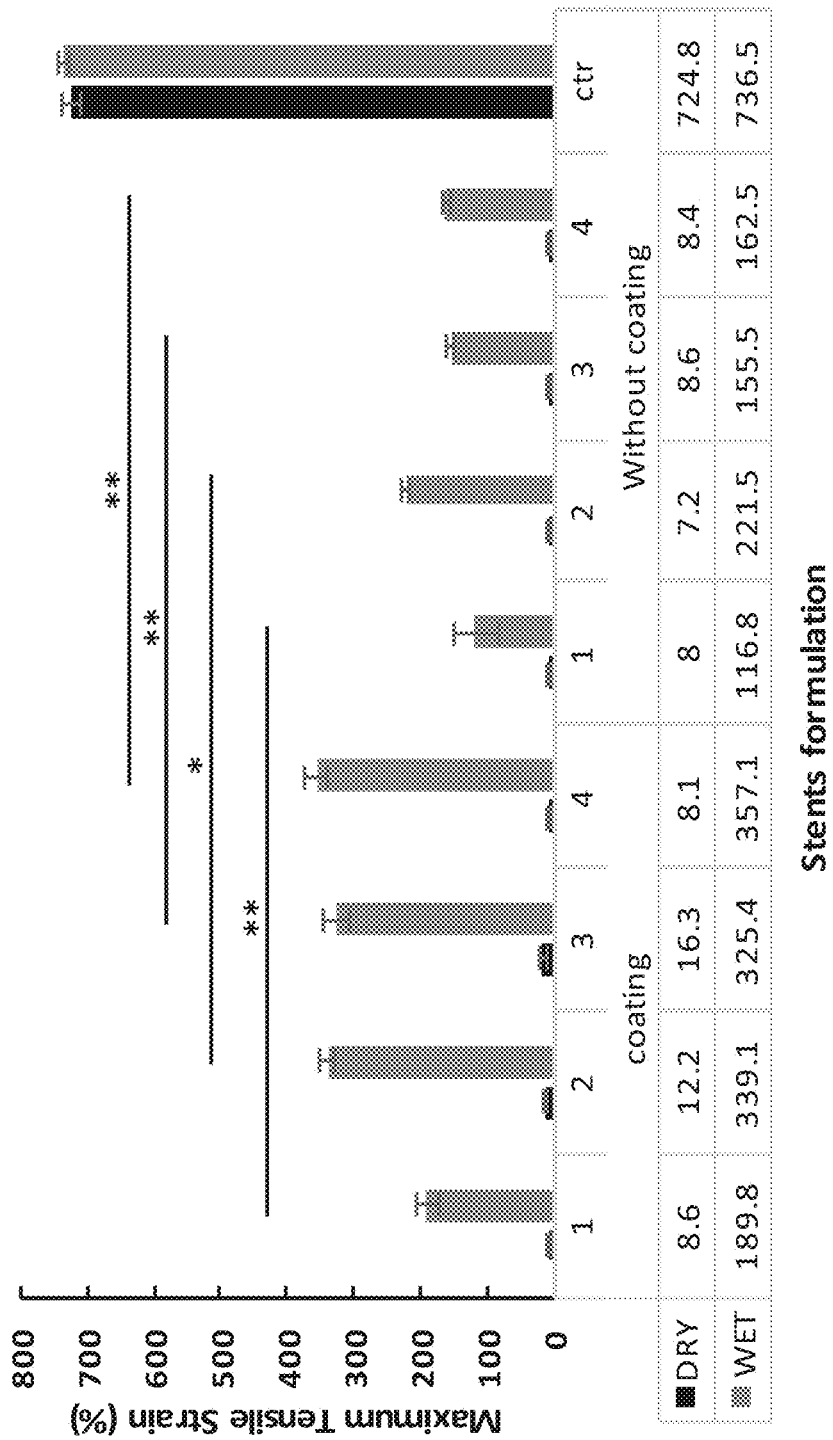
Figure 6C:
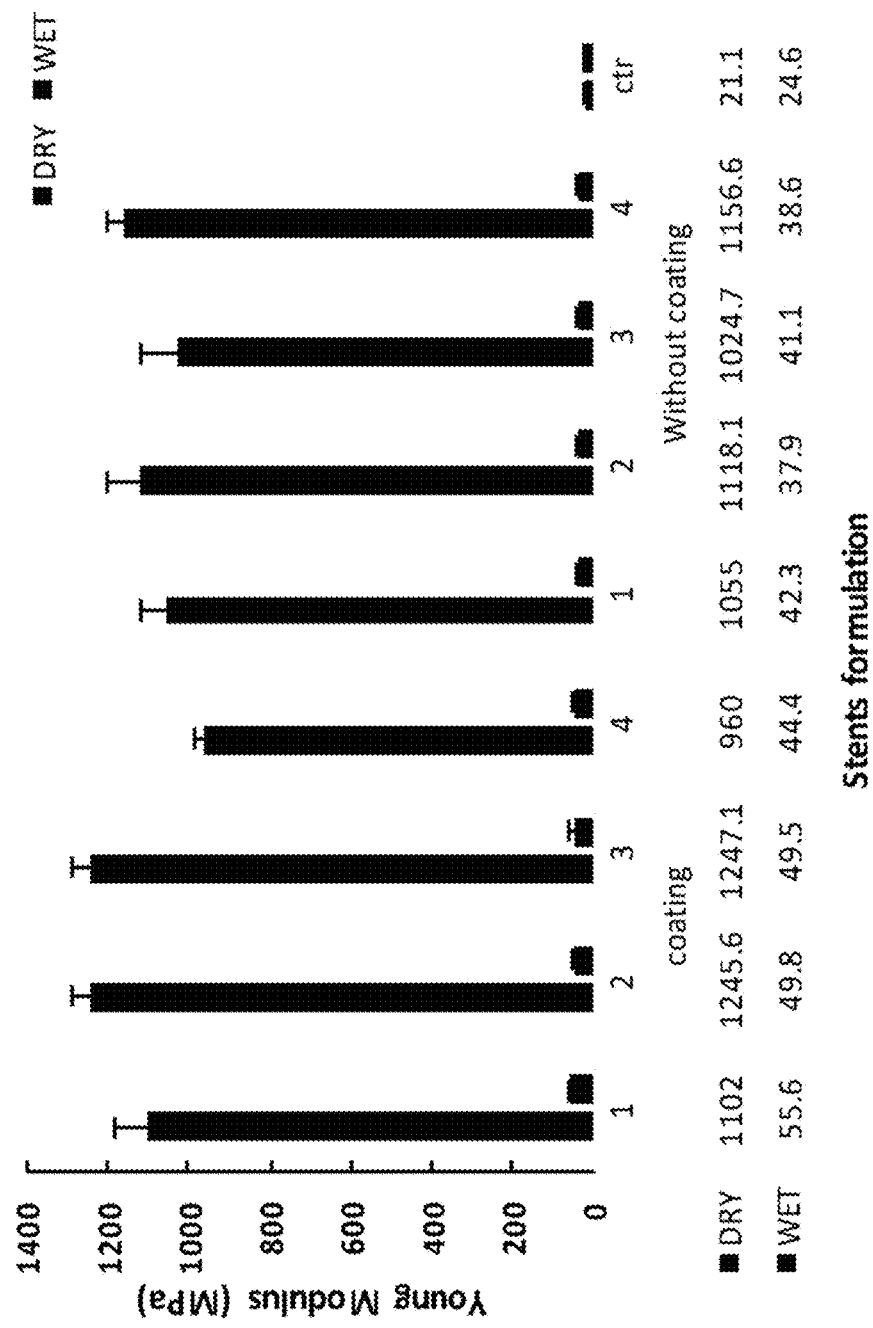
Figure 6D:
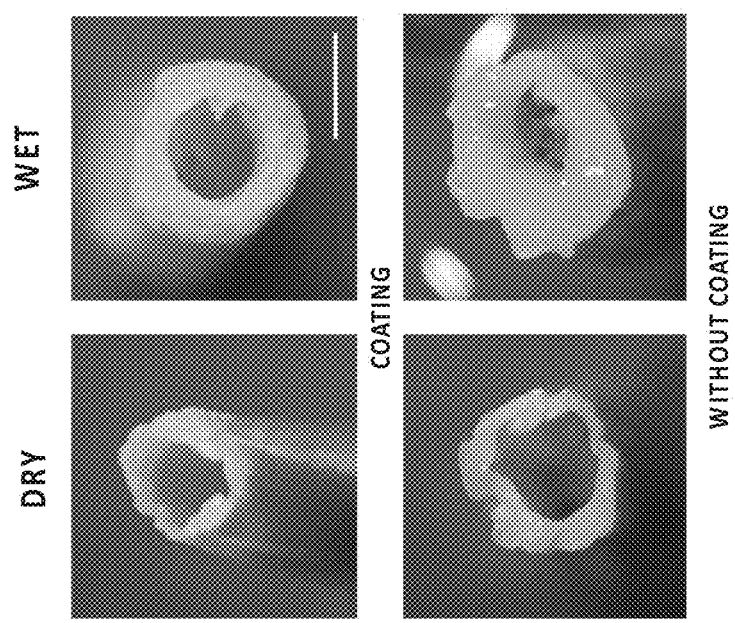

Leachables Cytotoxicity—The cytotoxicity of the leachables obtained from stent degradation was evaluated in accordance with the protocol described in ISO/EN 10.993 [19]. The viability of the cells cultured in a tissue culture plate, in the presence of the leachables, was determined as a function of the cells cultured in Dulbecco's modified Eagle medium (DMEM) culture medium. FIG. 5 presents the cell viability after 72 h in contact with the material dissolved in the culture medium. Significant differences were observed for the cell viability in the presence of the leachables in comparison with the latex, which was used as a positive control. The results demonstrate that there is no toxic interaction between the leachables from day 1 to day 9 and L929 cells.

Tensile mechanical tests—The tensile mechanical properties like maximum load (N), maximum tensile strain (%) and Young modulus (MPa) of the biodegradable ureteral stents developed are presented in FIGS. 6A-6D and FIGS. 7A-7D. FIGS. 6A-6D present the results in dry and wet state of the four different formulations of stents when using a concentration of 0.48M crosslinking agent. As a control the tensile results for the commercial stent (BIOSOFT® duo, Porges, Coloplast) are also presented. Comparing all studied formulations, significant differences were observed before and after hydration and with and without coating, in terms their mechanical properties. In all formulations and as expected of hydration in AUS (FIG. 6D) the values of tensile properties decrease in terms of Young modulus but increase in terms of maximum tensile strain. Furthermore, the ureteral stents after hydration become more elastic than in dry state. The results for the hydrated samples are far more important for the clinical purpose. Regarding the highest values, the maximum load was 78.7 N and in terms of Young modulus was 49.8 MPa after hydration for the coated stents of formulation 2. Comparing with 41.2 N and 24.6 MPa, respectively, for the commercial stent. On the other hand, in terms of maximum tensile strain (%) or elongation at break the control present values around 736.5% compared with 339.1% obtained for formulation 2. In general, the contribution of gelatine seems to increase the mechanical properties of the biodegradable stents. The hydration of the stents further contributes to increase the elasticity of the material.

Analyzing the effect of the PCL coating it also contributes to increase the elasticity and the ductility of the stents with significant differences. With the objective to study the influence of calcium ions concentration as crosslinking agent three different concentrations were tested with the formulation 2. This formulation was selected according the results obtained, due to the balance in terms of ductility and elasticity of biodegradable ureteral stent.

Figure 7A:
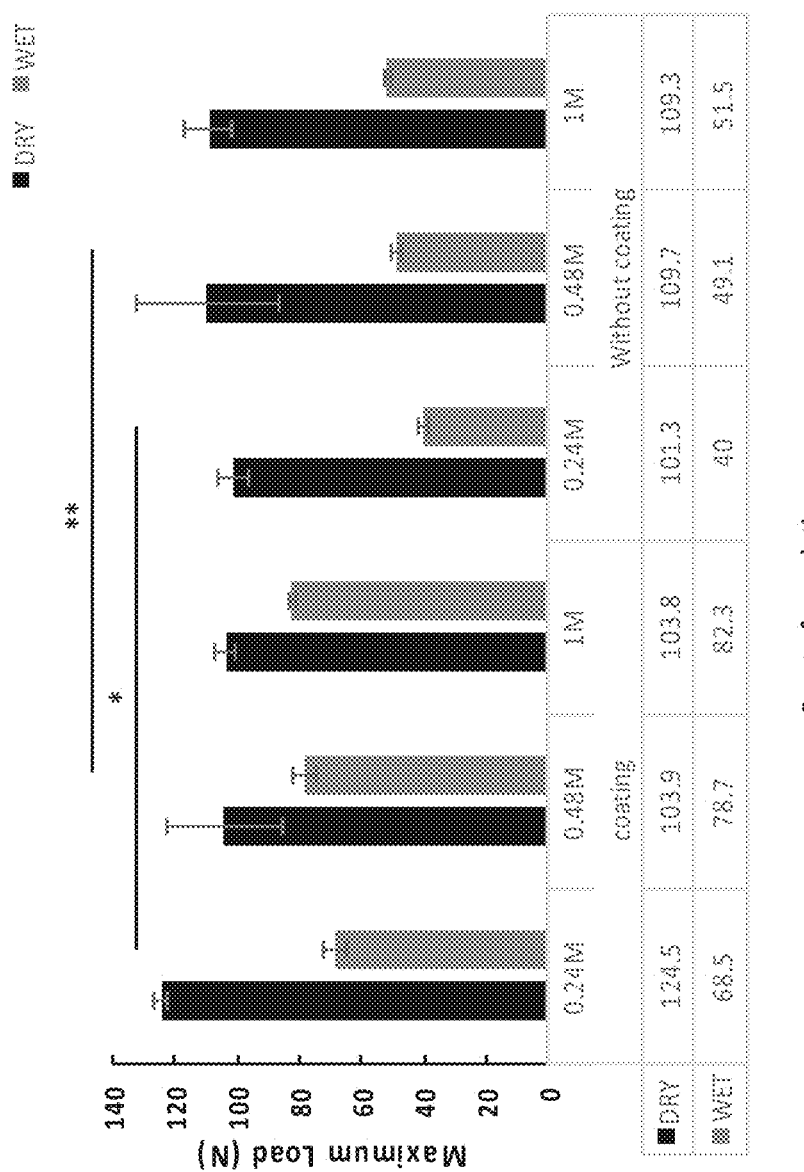
FIGS. 7A-7D. Mechanical properties of the biodegradable stents prepared with the formulation 2 with different concentrations of crosslinking agent before and after PCL coating in terms of maximum load (N) (FIG. 7A), maximum tensile strain (%) (FIG. 7B), young modulus (MPa) (FIG. 7C), and maximum tensile strain (%) of ureteral stent formulation 2 during the degradation time (FIG. 7D). Values are represented as average±SD, n=3. Statistical differences (*$p<0.05$, **$p<0.01$) using one way-ANOVA followed by a Tukey post-test.
Figure 7B:
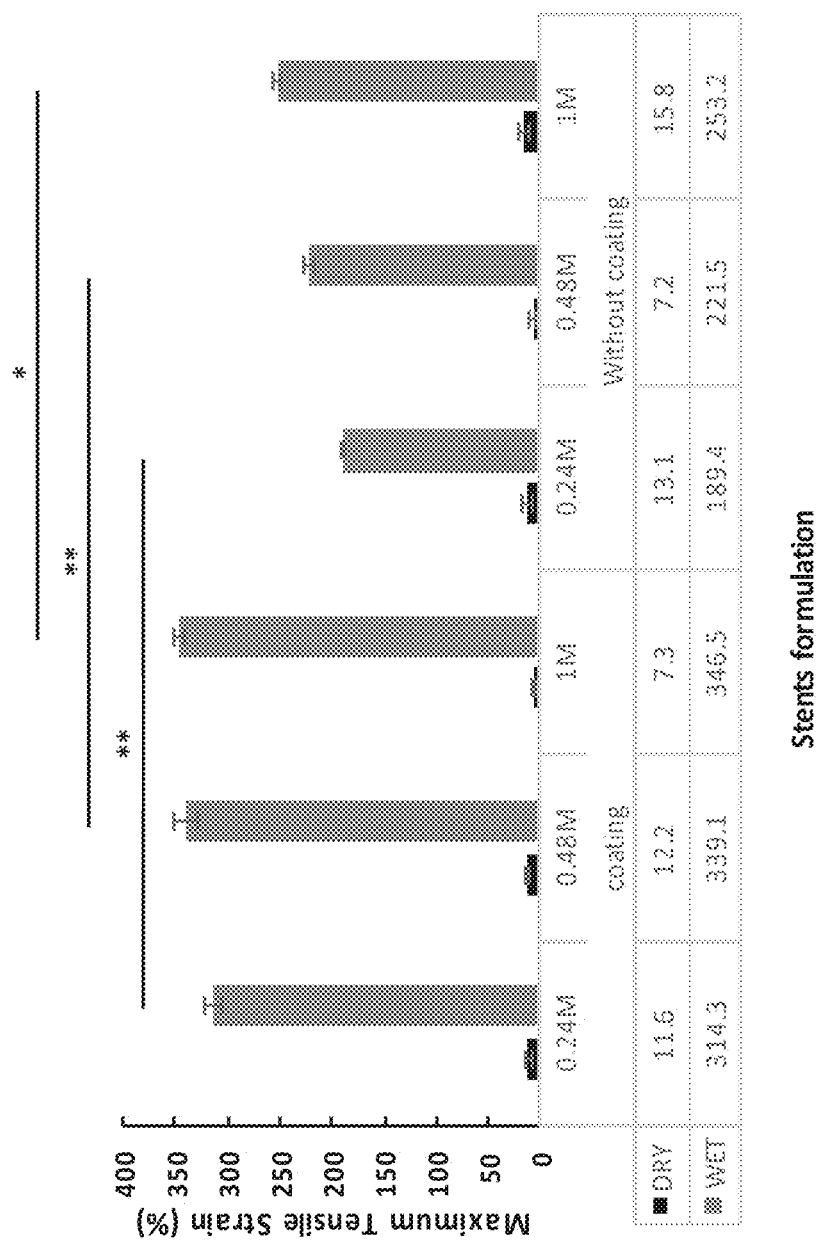
Figure 7C:
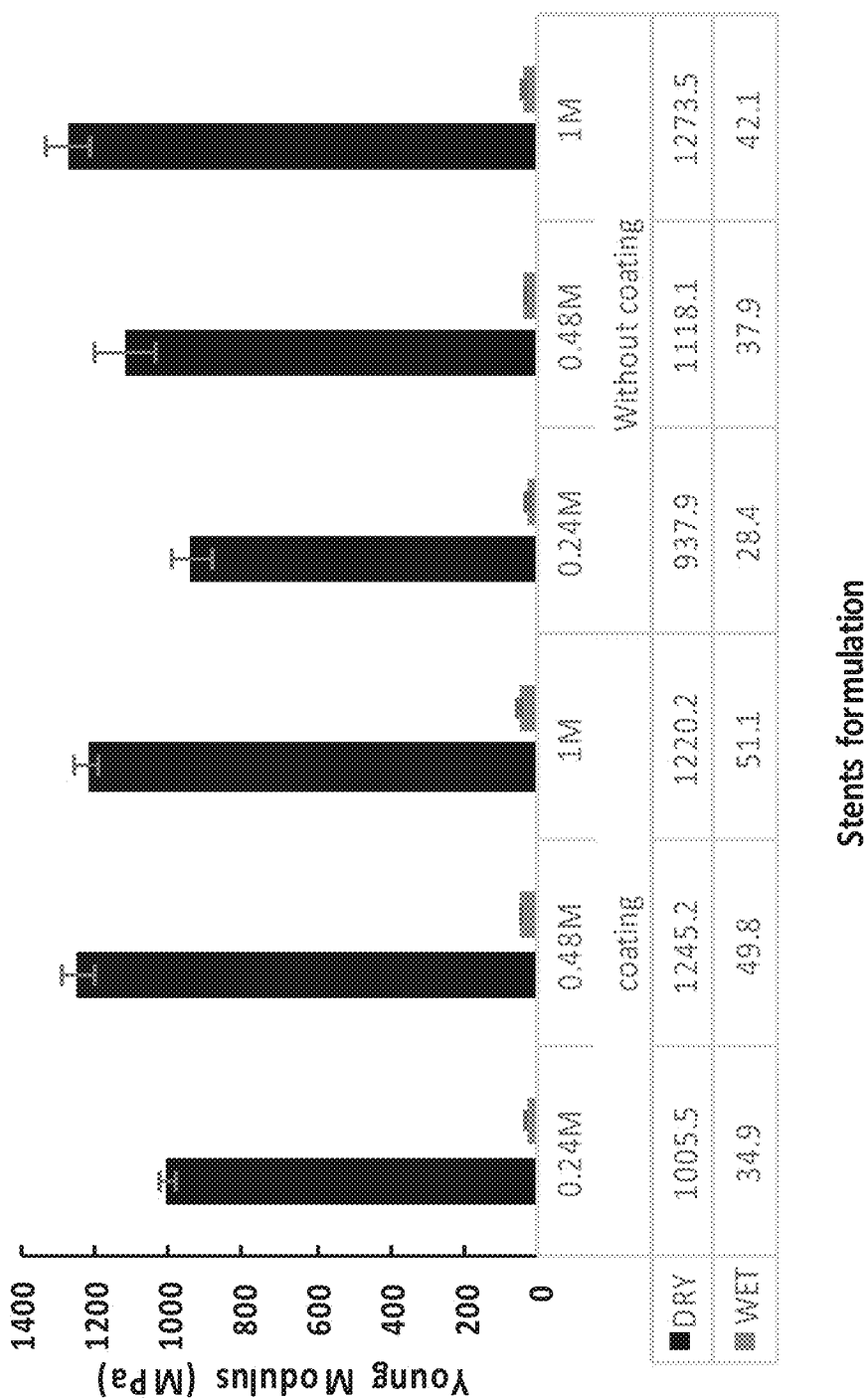
Figure 7D:
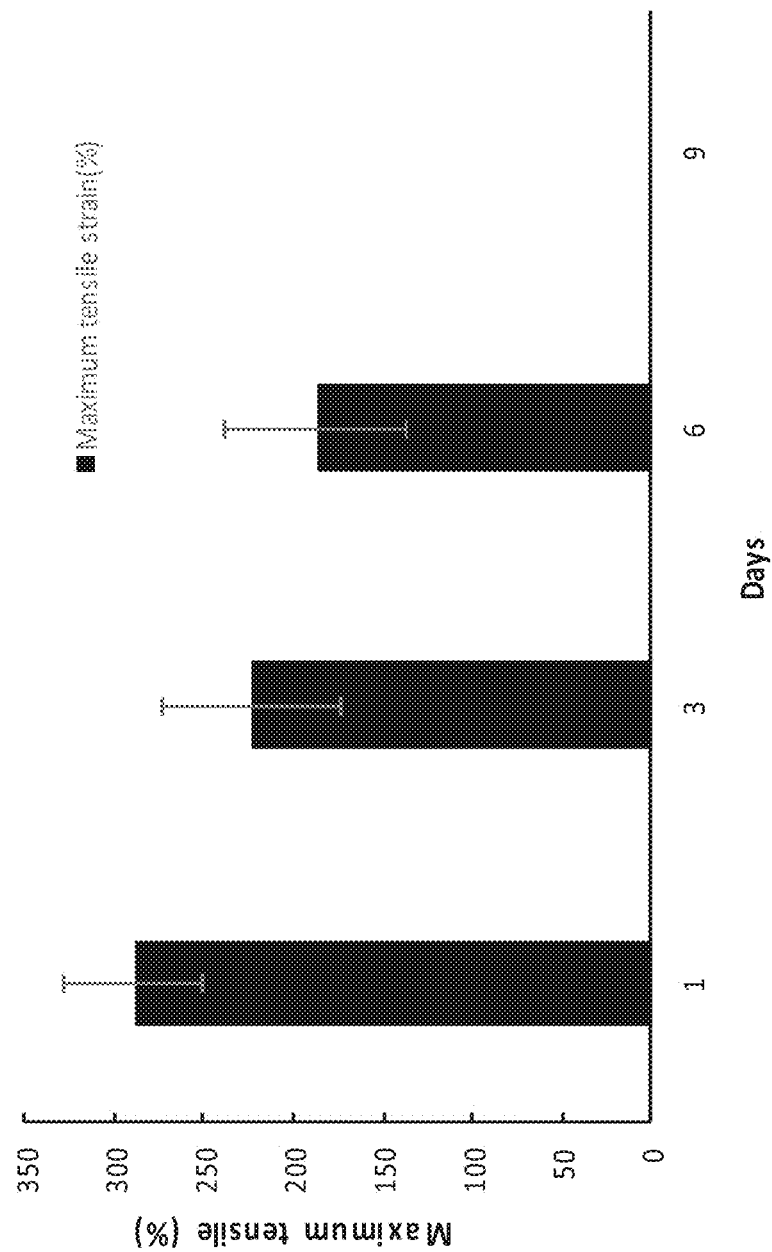
Figure 9:
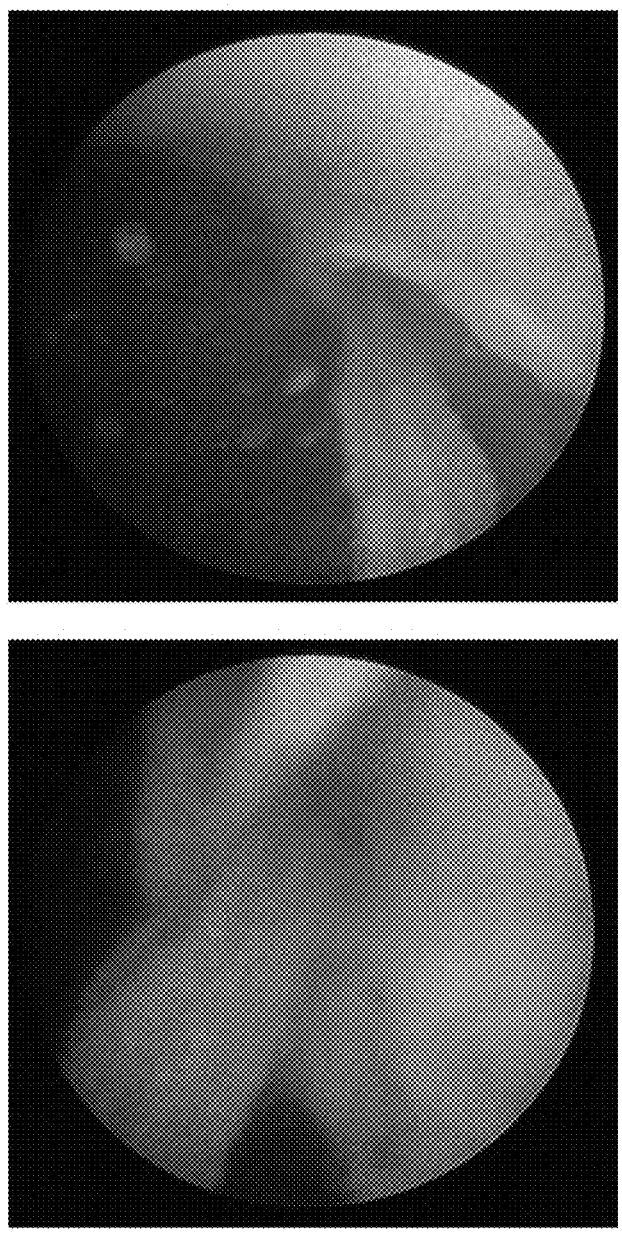
FIG. 9. Biodegradable ureteral stent crosslinked with genipin inside the right ostium pig ureter after 4 days of placement.

FIGS. 7A-C show herein the results for the ureteral biodegradable stent with formulation 2, using different concentrations of crosslinking agent, namely 0.24M, 0.48M and 1M. Comparing the different concentrations, the results suggest that the crosslinking concentration does not have a great impact in the final mechanical properties of the biodegradable ureteral stent. Although, a slight increase is observed increasing the calcium ions concentration. This was precisely reported in literature, ions increase the network linked, but in the present disclosure the concentration tested does not affect to much the mechanical properties of biodegradable ureteral stents [27].

The mechanical properties during the degradation process were measured (FIG. 7D) and the results show decrease of the mechanical properties during time of degradation. Nonetheless at day 6, before the complete degradation, the ureteral stent (formulation 2) shows an average maximum tensile near 200%. Although the mechanical properties decrease during the degradation process the properties seem to be enough to maintain the function of the ureteral stent before de total degradation. These observations are extremely important in the case there is the clinical need to remove the stents without compromising the obstruction of the ureter by possible fragments left.

In the first-generation of biodegradable ureteral stents made by natural polymer the values obtained were three times lower compared with the second-generation [16]. Clearly, increasing the gelatine concentration, the modification of the fabrication process and a incorporation of a new biodegradable coating allow the preparation of a biodegradable ureteral stent capable to be used in vivo following conventional ureteroscopy.

An ideal ureteral stent is expected to have adequate performance in terms of mechanical properties. Comparing the maximum tensile strain results with a resorbable ureteral stents made from PGA and PLGA [15,28] the natural origin materials here used present higher elongation comparing with the synthetic materials. In terms of global mechanical performance obtained in this study demonstrated to be similar or better than commercial stent available, BIOSOFT® duo, Porges, Coloplast.

In vivo Study in a porcine model—The validation in vivo of the biodegradable ureteral stents was performed in a different female domestic pigs. Conventional ureteroscopy was employed to implant the developed stents. The first stent tested in vivo was the first-generation of biodegradable ureteral stents based on natural origin polymers reported by Barros et al [20]. The first generation demonstrated upon surgical procedure the stents slipped perfectly into the cystoscope and the hydrophilic guidewire into the bladder through the urethra. The ureteral stent developed remains intact throughout the procedure and is not fragmented and proved easy removal if necessary. However, it was not ductile enough in order to be able to be positioned correctly in the ureter. On the contrary, this new second-generation of biodegradable ureteral stents, was successfully implanted in vivo. The biodegradable ureteral stents of this second-generation at formulation 2 were placed in the right ureters without any complication and as a control was placed stents commercials (BIOSOFT® duo, Porges, Coloplast) in the left ureters, following the conventional surgical procedure. In FIGS. 8A-8F it is possible to see the second generation of biodegradable stent placed in the ureters of the pig model. During the experiments all the animals remained asymptomatic and with a normal urine flow. After 3 days, an ureteroscopy was performed to the animals to evaluate the morphology of the ureters and the stents. The biodegradable stent remains intact with a great stability (FIG. 8C) and any undesired side effects was observed in ureters (FIG. 8D). At day 10, other ureteroscopy was performed and no fragments of the biodegradable ureteral stents were found and the morphology of the ureters remain normal without signs of inflammation or adverse reactions (FIGS. 8E and 8F). These biodegradable ureteral stents prepared from formulation 2 demonstrated to be intact during the first 3 days and after 10 days they are completely degraded and no stent residues were observed in the urinary trade. This experiment was repeated three times and all procedures lead to the same observation.

The experimental data show that a range of mixtures of alginate and gelatine and different concentrations of crosslinking agent are used to obtain a biodegradable ureteral stent from natural origin polymers which may be used for the treatment of urological disorders. In this second-generation of stents, it is possible see the radiopacicity, in wet state, of the biodegradable ureteral stent developed. The in vitro study show that higher concentration of gelatine in the biodegradable stent resulted in higher mechanical properties. Otherwise, higher concentration of alginate slower the degradation in vitro. The degradation products shown to be no cytotoxic and the degradation themselves shown to be homogenous. The second-generation of biodegradable ureteral stents developed shown could be implanted following the surgical procedure performed daily in the clinical practice. The ureteral stent remains intact during the first 3 days and after that starts to degrade. Full degradation is achieved after 10 days, with any presence of the stent materials inside the animal. The stents developed demonstrated to be safe and fulfilled the function of keeping the flow of urine from kidney to bladder while implanted in the ureter.

The present solution is not, obviously, in any way restricted to the herein described embodiments and a person with average knowledge in the area can predict many possibilities of modification of the same solution and substitutions of technical characteristics by others equivalent, depending on the requirements of each situation, as defined in the appended claims.

The embodiments described above can be combined with each other. The following claims further define the preferred embodiments of the present solution.

REFERENCES

[1] D. Lange, S. Bidnur, N. Hoag, B. H. Chew, Ureteral stent-associated complications[mdash] where we are and where we are going, Nat Rev Urol. 12 (2015) 17-25. doi:10.1038/nrurol.2014.340.

[2] C. E. Mendez-Probst, L. W. Goneau, K. W. MacDonald, L. Nott, S. Seney, C. N. Elwood, et al., The use of triclosan eluting stents effectively reduces ureteral stent symptoms: a prospective randomized trial, BJU Int. 110 (2012) 749-754. doi:10.1111/j.1464-410X.2011.10903.x.

[3] A. E. Krambeck, R. S. Walsh, J. D. Denstedt, G. M. Preminger, J. Li, J. C. Evans, et al., A Novel Drug Eluting Ureteral Stent: A Prospective, Randomized, Multicenter Clinical Trial to Evaluate the Safety and Effectiveness of a Ketorolac Loaded Ureteral Stent, J. Urol. 183 (2010) 1037-1043. doi:http://dx.doi.org/10.1016/j.juro.2009.11.035.

[4] E. N. Liatsikos, D. Karnabatidis, G. C. Kagadis, K. Rokkas, C. Constantinides, N. Christeas, et al., Application of paclitaxel-eluting metal mesh stents within the pig ureter: An experimental study, Eur. Urol. 51 (2007) 217-223. doi:DOI 10.1016/j.eururo.2006.05.054.

[5] E. O. Olweny, J. Landman, C. Andreoni, W. Collyer, K. Kerbl, M. Onciu, et al., Evaluation of the use of a biodegradable ureteral stent after retrograde endopyelotomy in a porcine model, J. Urol. 167 (2002) 2198-2202. doi:Unsp 0022-5347/02/1675-2198/0Doi 10.1016/S0022-5347(05)65128-2.

[6] A. Al-Aown, I. Kyriazis, P. Kallidonis, P. Kraniotis, C. Rigopoulos, D. Karnabatidis, et al., Ureteral stents: new ideas, new designs, Ther Adv Urol. 2 (2010) 85-92. doi:10.1177/1756287210370699.

[7] N. Venkatesan, S. Shroff, K. Jayachandran, M. Doble, Polymers as Ureteral Stents, J. Endourol. 24 (2010) 191-198. doi:DOI 10.1089/end.2009.0516.

[8] B. H. Chew, D. Lange, R. F. Paterson, K. Hendlin, M. Monga, K. W. Clinkscales, et al., Next Generation Biodegradable Ureteral Stent in a Yucatan Pig Model, J. Urol. 183 (2010) 765-771. doi:DOI 10.1016/j.juro.2009.09.073.

[9] J. E. Lingeman, D. A. Schulsinger, R. L. Kuo, Phase I trial of a temporary ureteral drainage stent, J. Endourol. 17 (2003) 169-171. doi:Doi 10.1089/089277903321618734.

[10] J. Lumiaho, A. Heino, V. Tunninen, M. Ala-Opas, M. Talja, T. Valimaa, et al., New bioabsorbable polylactide ureteral stent in the treatment of ureteral lesions: An experimental study, J. Endourol. 13 (1999) 107-112. doi:DOI 10.1089/end.1999.13.107.

[11] J. Lumiaho, A. Heino, T. Kauppinen, M. Talja, E. Alhava, T. Valimaa, et al., Drainage and antireflux characteristics of a biodegradable self-reinforced, self-expanding X-ray-positive ploy-L,D-lactide spiral partial Ureteral stent: An experimental study, J. Endourol. 21 (2007) 1559-1564. doi:DOI 10.1089/end.2005.0085.

[12] J. Lumiaho, A. Heino, T. Pietilainen, M. Ala-Opas, M. Talja, T. Valimaa, et al., The morphological, in situ effects of a self-reinforced bioabsorbable polylactide (SR-PLA 96) ureteric stent; An experimental study, J. Urol. 164 (2000) 1360-1363. doi:Doi 10.1016/S0022-5347(05)67199-6.

[13] M. Talja, M. Multanen, T. Valimaa, P. Tormala, Bioabsorbable SR-PLGA horn stent after antegrade endopyelotomy: A case report, J. Endourol. 16 (2002) 299-302. doi:Doi 10.1089/089277902760102785.

[14] J. Lumiaho, A. Heino, S. Aaltomaa, T. Valimaa, M. Talja, A short biodegradable helical spiral ureteric stent provides better antireflux and drainage properties than a double-J stent, Scand. J. Urol. Nephrol. 45 (2011) 129-133. doi:Doi 10.3109/00365599.2010.544673.

[15] T. Zou, L. Wang, W. C. Li, W. Z. Wang, F. Chen, M. W. King, A resorbable bicomponent braided ureteral stent with improved mechanical performance, J. Mech. Behav. Biomed. Mater. 38 (2014) 17-25. doi:DOI 10.1016/j.jmbbm.2014.06.004.

[16] A. A. Barros, A. Rita, C. Duarte, R. A. Pires, B. Sampaio-Marques, P. Ludovico, et al., Bioresorbable ureteral stents from natural origin polymers, J. Biomed. Mater. Res. Part B Appl. Biomater. 103 (2015) 608-617. doi:10.1002/jbm.b.33237.

[17] R. W. Schlick, K. Planz, Potentially useful materials for biodegradable ureteric stents, Br. J. Urol. 80 (1997) 908-910. doi:DOI 10.1046/j.1464-410X.1997.00484.x.

[18] A. Khandwekar, M. Doble, Physicochemical characterisation and biological evaluation of polyvinylpyrrolidone-iodine engineered polyurethane, J. Mater. Sci. Mater. Med. 22 (2011) 1231-1246. doi:10.1007/s10856-011-4285-8.

[19] ISO/10993, Biological Evaluation of Medical Devices. Part 5. Test for Cytotoxicity In Vitro Methods: 8.2 Test on Extracts, (1992).

[20] E. Lima, C. Rolanda, L. Osório, J. M. Pêgo, D. Silva, T. Henriques-Coelho, et al., Endoscopic closure of transmural bladder wall perforations, Eur. Urol. 56 (2009) 151-7. doi:10.1016/j.eururo.2008.06.010.

[21] J. E. Lingeman, G. M. Preminger, Y. Berger, J. D. Denstedt, L. Goldstone, J. W. Segura, et al., Use of a temporary ureteral drainage stent after uncomplicated ureteroscopy: Results from a phase II clinical trial, J. Urol. 169 (2003) 1682-1688. doi:DOI 10.1097/01.ju.0000055600.18515.a1.

[22] A. R. C. Duarte, V. E. Santo, A. Alves, S. S. Silva, J. Moreira-Silva, T. H. Silva, et al., Unleashing the Potential of Supercritical Fluids for Polymer Processing in Tissue Engineering and Regenerative Medicine, J. Supercrit. Fluids. (2013).

[23] H. J. Kong, D. Kaigler, K. Kim, D. J. Mooney, Controlling Rigidity and Degradation of Alginate Hydrogels via Molecular Weight Distribution, Biomacromolecules. 5 (2004) 1720-1727. doi:10.1021/bm049879r.

[24] A. Blandino, M. Macias, D. Cantero, Formation of calcium alginate gel capsules: Influence of sodium alginate and $CaCl_2$) concentration on gelation kinetics, J. Biosci. Bioeng. 88 (1999) 686-689. doi:http://dx.doi.org/10.1016/S1389-1723(00)87103-0.

[25] A. Jejurikar, G. Lawrie, D. Martin, L. Grondahl, A novel strategy for preparing mechanically robust ionically cross-linked alginate hydrogels, Biomed Mater. 6 (2011). doi:Artn 025010Doi 10.1088/1748-6041/6/2/025010.

[26] B. Mohanty, H. B. Bohidar, Microscopic structure of gelatin coacervates, Int. J. Biol. Macromol. 36 (2005) 39-46. doi:DOI 10.1016/j.ijbiomac.2005.03.012.

[27] A. D. Augst, H. J. Kong, D. J. Mooney, Alginate Hydrogels as Biomaterials, Macromol. Biosci. 6 (2006) 623-633. doi:10.1002/mabi.200600069.

[28] M. Q. Zhang, T. Zou, Y. C. Huang, Y. F. Shang, G. G. Yang, W. Z. Wang, et al., Braided thin-walled biodegradable ureteral stent: Preliminary evaluation in a canine model, Int. J. Urol. 21 (2014) 401-407. doi:10.1111/iju.12297.

The invention claimed is:

1. A stent comprising:
a polymeric substrate, wherein the polymeric substrate comprises 30% (w/w) of alginate, 65% (w/w) of gelatine, and 5% (w/w) of contrast agent bismuth (III) carbonate; and
a polymeric biodegradable resin for coating the polymeric substrate, wherein the polymeric biodegradable resin comprises polycaprolactone resin.

2. The stent of claim 1, wherein the polymeric biodegradable resin further comprises at least one polymer biodegradable resin selected from the group consisting of polyglycolide, poly(lactic-co-glycolic acid with lactic acid), poly (glycolide-co-caprolactone) with ε-caprolactone, poly (glycolide-co-trimethylene carbonate) with trimethylene carbonate, and mixtures thereof.

3. The stent of claim 1, wherein the stent is a ureteral stent.

4. A stent comprising:
a polymeric substrate wherein the polymeric substrate is formed by:
(1) combining 30% (w/w) alginate, 65% (w/w) gelatine, and 5% (w/w) contrasting agent bismuth (Ill) carbonate, and
(2) adding a crosslinking agent; and
a polymeric biodegradable resin for coating the polymeric substrate formed in step (2), wherein the polymeric biodegradable resin comprises polycaprolactone resin.

5. The stent of claim 4, wherein the crosslinking agent is a chemical crosslinker comprising a functional group able to react with gelatine amines.

6. The stent of claim 4, wherein the crosslinking agent is an ionic crosslinking agent comprising monovalent or divalent ions in which the cation is selected from the group consisting of calcium, magnesium, barium, strontium, boron, beryllium, aluminium, iron, copper, cobalt, lead and silver, and the anion is selected from the group consisting of chloride, nitrate, phosphate, citrate, borate, succinate, maleate oxalate, and mixtures thereof.

7. The stent of claim 4, wherein the crosslinking agent is selected from a group consisting of: calcium chloride, genipin, glutaraldeyhyde, carbodiimides, and mixtures thereof.

8. The stent of claim 4, further comprising a therapeutic agent which is added to either the polymeric substrate or the polymeric biodegradable resin, wherein the therapeutic agent is selected from the group consisting of: an anti-inflammatory agent, an anti-microbial agent, an anti-cancer agent, an antiviral agent, and mixtures thereof.

9. The stent of claim 8, wherein the anti-inflammatory agent is selected from the group consisting of: prednisolone, methylprednisolone, fluorometholone, dexamethasone, betamethasone, hydrocortisone, medrysone, loteprednol, rimexolone, triamcinolone, diclofenac, ketorolac, flurbiprofen, indomethacin, suprofen, ibuprofen, ketorolac tromethamine, emedastine, levocabastine, azelastine, olopatadine, ketotifen, ketoprofen, cromolyn, iodoxamide, and mixtures thereof.

10. The stent of claim 8, wherein the anti-microbial agent is selected from the group consisting of: amoxicillin, dicloxacillin, augmentin, cephalosporins, gentamycin, tobramycin, neomycin, erythromycin, azithromycin, clarithromycin, ofloxacin, ciprofloxacin, norfloxacin, levofloxacin, and mixtures thereof.

11. The stent of claim 8, wherein the anti-cancer agent is selected from the group consisting of: methotrexate, vinblastine, doxorubicin, cisplatin, granulocyte colony-stimulating factor, gemcitabine, carboplatin, 5-fluorouracil, ifosfamide, pemetrexed, paclitaxel, epirubicin, mitomycin C, capecitabine, *Bacillus* Calmette-Guerin (BCG), and mixtures thereof.

12. The stent of claim 8, wherein the antiviral agent is selected from the group consisting of: acyclovir, valacyclovir, famciclovir, and mixtures thereof.

13. The stent of claim 8, wherein the therapeutic agent is added to the polymeric substrate.

14. The stent of claim 8, wherein the therapeutic agent is added to in the polymeric biodegradable resin.

* * * * *